(12) United States Patent
Nakayama

(10) Patent No.: US 10,954,183 B2
(45) Date of Patent: Mar. 23, 2021

(54) CURABLE COMPOSITION, SEMI-CURED PRODUCT, CURED PRODUCT, OPTICAL MEMBER, LENS, AND COMPOUND

(71) Applicant: FUJIFILM Corporation, Tokyo (JP)

(72) Inventor: Takafumi Nakayama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/715,952

(22) Filed: Dec. 16, 2019

(65) Prior Publication Data

US 2020/0115316 A1   Apr. 16, 2020

Related U.S. Application Data

(63) Continuation of application No. PCT/JP2018/022517, filed on Jun. 13, 2018.

(30) Foreign Application Priority Data

Jun. 23, 2017   (JP) .............................. JP2017-123582

(51) Int. Cl.
*C07C 69/54*     (2006.01)
*C07C 69/604*    (2006.01)
*G02B 1/04*      (2006.01)

(52) U.S. Cl.
CPC ............ *C07C 69/54* (2013.01); *C07C 69/604* (2013.01); *G02B 1/04* (2013.01)

(58) Field of Classification Search
CPC ..... C07C 69/54; C07C 69/604; C07C 69/612; G02B 1/04
See application file for complete search history.

(56) References Cited

U.S. PATENT DOCUMENTS

| | | | |
|---|---|---|---|
| 2013/0237630 A1 | 9/2013 | Morooka et al. | |
| 2015/0175731 A1* | 6/2015 | Saitoh | C07C 317/22 359/642 |
| 2019/0338157 A1* | 11/2019 | Kouno | C09D 4/00 |

FOREIGN PATENT DOCUMENTS

| | | | |
|---|---|---|---|
| JP | H03-067201 A | 3/1991 | |
| JP | H05-034647 A | 2/1993 | |
| JP | H05-061006 A | 3/1993 | |
| JP | H05-271316 A | 10/1993 | |
| JP | H08-208776 A | 8/1996 | |
| JP | H09-012642 A | 1/1997 | |
| JP | 2008-137938 A | 6/2008 | |
| JP | 2009-126011 A | 6/2009 | |
| JP | 2012-107191 A | 6/2012 | |
| JP | 2012-167019 A | 9/2012 | |
| JP | 2014-043565 A | 3/2014 | |
| JP | 6327408 * | 4/2018 | ............. C08F 20/16 |
| WO | 2016/111923 A1 | 7/2016 | |
| WO | 2016/111925 A1 | 7/2016 | |

OTHER PUBLICATIONS

International Search Report issued in PCT/JP2018/022517; dated Jul. 24, 2018.
International Preliminary Report on Patentability and Written Opinion Issued in PCT/JP2018/022517; dated Dec. 24, 2019.
An Office Action mailed by the Japanese Patent Office dated Jan. 5, 2021, which corresponds to Japanese Patent Application No. 2019-525475 and is related to U.S. Appl. No. 16/715,952.

\* cited by examiner

*Primary Examiner* — Yate' K Cutliff
(74) *Attorney, Agent, or Firm* — Studebaker & Brackett PC

(57) ABSTRACT

An object of the present invention is to develop a compound and a curable composition which are capable of providing an optical member having favorable refractive index characteristics and a high degree of moisture-heat resistance. The present invention relates to a compound represented by General Formula (1), a curable composition containing the compound, a semi-cured product, a cured product, an optical member, and a lens. At least one of $R^1$, ..., or $R^5$ represents an aryl group or a heteroaryl group which is substituted by a substituent containing a (meth)acryloyloxy group, and at least one of $R^6$, ..., or $R^{10}$ represents an aryl group or a heteroaryl group.

General Formula (1)

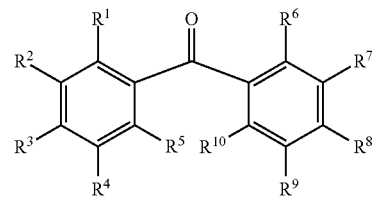

17 Claims, No Drawings

CURABLE COMPOSITION, SEMI-CURED PRODUCT, CURED PRODUCT, OPTICAL MEMBER, LENS, AND COMPOUND

CROSS-REFERENCE TO RELATED APPLICATIONS

This application is a Continuation of PCT International Application No. PCT/JP2018/022517 filed on Jun. 13, 2018, which claims priority under 35 U.S.C § 119(a) to Japanese Patent Application No. 2017-123582 filed on Jun. 23, 2017. Each of the above application(s) is hereby expressly incorporated by reference, in its entirety, into the present application.

BACKGROUND OF THE INVENTION

1. Field of the Invention

The present invention relates to a curable composition, a semi-cured product and a cured product which are obtained by curing the curable composition, an optical member and a lens which include the cured product, and a compound used in the curable composition.

2. Description of the Related Art

In the related art, glass materials have been used for an optical member of an imaging module such as a camera, a video camera, a mobile phone with a camera, a video phone, or a door phone with a camera. Glass materials have been used preferably because they have various optical characteristics and excellent environmental resistance, but they have a disadvantage in that weight reduction and miniaturization are not easy and workability or productivity is poor. In contrast, because a resin cured product can be produced in a massive amount and has excellent workability, it has recently been used in various optical members.

In recent years, in accordance with miniaturization of an imaging module, a size of an optical member used in the imaging module is required to be reduced, but in a case of miniaturizing an optical member, a problem of chromatic aberration occurs. For this reason, in an optical member formed of a cured resin, studies have been conducted regarding adjusting an Abbe number (vd) and a partial dispersion ratio (θg, F) by adding various additives to a curable composition to change characteristics of a product after curing, and then correcting chromatic aberration.

JP2012-167019A discloses a compound that can provide an optical member having a high Abbe number (vd) and a high partial dispersion ratio (θg, F). It is disclosed that this compound has a 4,4'-bis(aryl)diphenylsulfone skeleton, and is used in the manufacture of compound lenses by incorporating the compound itself in a matrix polymer, or polymerizing or copolymerizing the compound.

Meanwhile, regarding a compound having a skeleton similar to the 4,4'-bis(aryl)diphenylsulfone skeleton, its refractive index characteristics and applications to optical members are hardly studied. For example, WO2016/111923 discloses a compound having a 4,4'-bis(piperazino)dibenzophenone skeleton, but this document merely discloses its usefulness as a photopolymerization initiator, and does not mention regarding its usefulness as a compound for optical members.

SUMMARY OF THE INVENTION

The inventors of the present invention have conducted additional tests on the optical member disclosed in JP2012-167019A, and have found that there is a problem of moisture-heat resistance in a case where the optical member is placed under high temperature and high humidity. Since lenses may be used under high temperature and high humidity depending on elements or devices to which lenses are mounted, the problem of moisture-heat resistance means that applications for lenses are greatly restricted. In addition, regarding the similar compound disclosed in WO2016/111923, because of its structure, this compound is also expected to have the problem of moisture-heat resistance and poor refractive index characteristics.

In order to solve such problems of the related art, the inventors of the present invention have conducted intensive studies to develop an optical member having excellent refractive index characteristics as well as excellent moisture-heat resistance, and to develop a compound and a curable composition which are capable of providing such an optical member.

As a result of intensive studies, the inventors of the present invention have found that, in a case where a compound having a bis(aryl)benzophenone skeleton is used, it is possible to provide an optical member having excellent moisture-heat resistance as well as favorable refractive index characteristics. As a result, the following inventions have been provided as specific means for solving the above-described problems.

[1] A curable composition comprising a compound represented by General Formula (1).

General Formula (1)

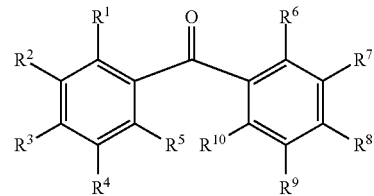

In General Formula (1), $R^1$ to $R^{10}$ each independently represent a hydrogen atom or a substituent, at least one of $R^1$, ..., or $R^5$ is an aryl group substituted by a substituent containing a (meth)acryloyloxy group or a heteroaryl group substituted by a substituent containing a (meth)acryloyloxy group, and at least one of $R^6$, ..., or $R^{10}$ is a substituted or unsubstituted aryl group or a substituted or unsubstituted heteroaryl group.

$R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, and $R^9$ and $R^{10}$ each may be bonded to each other to form a linking group necessary to form a cyclic structure. Where, a molecule represented by General Formula (1) does not include a polycyclic structure in which three or more aromatic rings are condensed.

[2] The curable composition according to [1], in which at least one of $R^6$, ..., or $R^{10}$ is an aryl group substituted by a substituent containing a (meth)acryloyloxy group or a heteroaryl group substituted by a substituent containing a (meth)acryloyloxy group.

[3] The curable composition according to [1], in which the compound is represented by General Formula (2).

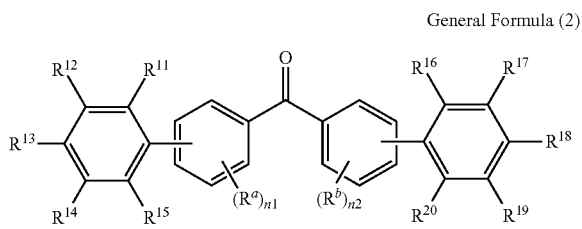

General Formula (2)

In General Formula (2), $R^a$ and $R^b$ each independently represent a substituent other than an aryl group and a heteroaryl group, n1 and n2 each independently represent an integer of 0 to 4, in which in a case where n1 is 2 or more, a plurality of $R^a$'s may be the same as or different from each other, and in a case where n2 is 2 or more, a plurality of $R^b$'s may be the same as or different from each other, $R^{11}$ to $R^{20}$ each independently represent a hydrogen atom or a substituent, and at least one of $R^{11}$, ..., or $R^{15}$ is a substituent containing a (meth)acryloyloxy group.

$R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, and $R^{19}$ and $R^{20}$; two $R^a$'s respectively bonded to adjacent cyclic-skeleton-forming atoms of a benzene ring; and two $R^b$'s respectively bonded to adjacent cyclic-skeleton-forming atoms of a benzene ring each may be bonded to each other to form a linking group necessary to form a cyclic structure. Where, a molecule represented by General Formula (2) does not include a polycyclic structure in which three or more aromatic rings are condensed.

[4] The curable composition according to [1], in which the compound is represented by General Formula (3).

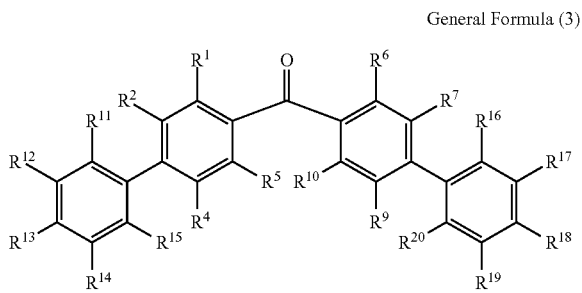

General Formula (3)

In General Formula (3), $R^1$, $R^2$, $R^4$, $R^5$, $R^6$, $R^7$, $R^9$, and $R^{10}$ each independently represent a hydrogen atom or a substituent other than an aryl group and a heteroaryl group, $R^{11}$ to $R^{20}$ each independently represent a hydrogen atom or a substituent, and at least one of $R^{11}$, ..., or $R^{15}$ is a substituent containing a (meth)acryloyloxy group. $R^1$ and $R^2$, $R^4$ and $R^5$, $R^6$ and $R^7$, $R^9$ and $R^{10}$, $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, and $R^{19}$ and $R^{20}$ each may be bonded to each other to form a linking group necessary to form a cyclic structure. Where, a molecule represented by General Formula (3) does not include a polycyclic structure in which three or more aromatic rings are condensed.

[5] The curable composition according to [3] or [4], in which $R^{12}$ is a substituent containing a (meth)acryloyloxy group.

[6] The curable composition according to any one of [3] to [5], in which at least one of $R^{16}$, or $R^{20}$ is a substituent containing a (meth)acryloyloxy group.

[7] The curable composition according to any one of [3] to [6], in which $R^{11}$, $R^{15}$, $R^{16}$, and $R^{20}$ are hydrogen atoms.

[8] The curable composition according to any one of [1] to [7], in which the substituent containing a (meth)acryloyloxy group is represented by General Formula (4).

$$Ac(-L^1-L^2)_{m1}(-L^3)_{m2}-*$$ General Formula (4)

In General Formula (4),

Ac represents a (meth)acryloyloxy group, $L^1$ represents an alkylene group that has 1 to 6 carbon atoms and may have a substituent, $L^2$ represents a carbonyl group, an ether group, a thiocarbonyl group, a thioether group, or a linking group that is a combination of these groups, $L^3$ represents an alkylene group that has 1 to 6 carbon atoms and may have a substituent, m1 represents any integer of 0 to 10, in which in a case where m1 is 2 or more, a plurality of $L^1$'s may be the same as or different from each other, and a plurality of $L^2$'s may be the same as or different from each other, m2 represents 0 or 1, and

* represents a binding site of a substituent containing a (meth)acryloyloxy group.

[9] The curable composition according to [8], in which the substituent containing a (meth)acryloyloxy group is a (meth)acryloyloxyalkoxy group, a (meth)acryloyloxyalkoxyalkyl group, a (meth)acryloyloxyalkoxycarbonylalkyl group, a (meth)acryloyloxyalkoxycarbonylacyloxy group, or a (meth)acryloyloxyalkoxycarbonylacyloxyalkyl group.

[10] The curable composition according to any one of [1] to [9], in which the compound contains two or more substituents containing a (meth)acryloyloxy group in a molecule.

[11] The curable composition according to any one of [1] to [10], in which the compound does not contain a polycyclic structure in which two or more aromatic rings are condensed in a molecule.

[12] The curable composition according to any one of [1] to [11], in which the curable composition contains at least one selected from a photoradical polymerization initiator or a thermal radical polymerization initiator.

[13] A semi-cured product of the curable composition according to any one of [1] to [12].

[14] A cured product of the curable composition according to any one of [1] to [12].

[15] An optical member comprising the cured product according to [14].

[16] A lens comprising the cured product according to [14].

[17] A compound represented by General Formula (2).

In a case where a compound represented by General Formula (1) or a curable composition containing the compound represented by General Formula (1) is used, it is possible to provide an optical member having favorable refractive index characteristics and excellent moisture-heat resistance.

DESCRIPTION OF THE PREFERRED EMBODIMENTS

Hereinafter, the present invention will be described in detail. The description of constituent elements described below can be made based on representative embodiments and specific examples, but the present invention is not limited to such embodiments.

DESCRIPTION OF TERMS

First, terms and symbols used in the present specification will be explained.

Numerical ranges expressed using "to" in the present specification mean a range including numerical values described before and after "to" as the lower limit and the upper limit.

In the indication of a group in the present specification, the indication not including substitution or unsubstitution includes those having a substituent and also those not having a substituent. That is, unless it is described as "unsubstituted", those having no substituent and those having a substituent are also included. For example, an "alkyl group" refers not only to an alkyl group not having a substituent (unsubstituted alkyl group) but also an alkyl group having a substituent (substituted alkyl group). Furthermore, in a case where the carbon number of the group is described, the carbon number means the total carbon numbers including the carbon number of the substituent substituted on the group. For example, in a case where the carbon number of an alkyl group is described, it means the total carbon numbers including the carbon number of the substituent substituted on the alkyl group.

In the present specification, "(meth)acrylate" represents acrylate and methacrylate, and "(meth)acryloyloxy" represents acryloyloxy and methacryloyloxy.

In the present specification, the "substituent" means a monovalent atom other than a hydrogen atom or a monovalent atomic group. Preferable substituents include a halogen atom, a hydroxyl group, an alkyl group, an alkenyl group, an alkoxy group, an alkylthio group, an acyl group, an acyloxy group, an alkoxycarbonyl group, an aryl group, a heteroaryl group, an aryloxy group, a heteroaryloxy group, an aryloxycarbonyl group, a heteroaryloxycarbonyl group, an arylthio group, a heteroarylthio group, a cyano group, and an amino group. More preferable substituents include a hydroxyl group, an alkyl group, an alkoxy group, and an alkylthio group.

In the present specification, the "halogen atom" is preferably a fluorine atom, a chlorine atom, a bromine atom or an iodine atom.

In the present specification, the "alkyl group" may be linear, branched, or cyclic. Furthermore, two or more of a linear chain portion, a branched portion, and a cyclic portion may be mixed. A linear chain or branched alkyl group is preferable. The carbon number of the alkyl group can be, for example, 1 or more, 2 or more, 4 or more, or 6 or more. Furthermore, the carbon number can be 30 or less, 20 or less, or 10 or less. Specific examples of alkyl groups include a methyl group, an ethyl group, an n-propyl group, an isopropyl group, an n-butyl group, an isobutyl group, a t-butyl group, an n-pentyl group, an isopentyl group, an n-hexyl group, an isohexyl group, a 2-ethylhexyl group, a cyclopentyl group, a cyclohexyl group, and a cycloheptyl group.

In the present specification, the "alkenyl group" may be linear, branched, or cyclic. Furthermore, two or more of a linear chain portion, a branched portion, and a cyclic portion may be mixed. A linear chain or branched alkenyl group is preferable. The carbon number of the alkenyl group can be, for example, 2 or more, 4 or more, or 6 or more. Furthermore, the carbon number can be 30 or less, 20 or less, or 10 or less. Specific examples of alkenyl groups include an ethenyl group, an n-propenyl group, an isopropenyl group, an n-butenyl group, an isobutenyl group, a t-butenyl group, an n-pentenyl group, an isopentenyl group, an n-hexenyl group, an isohexenyl group, a 2-ethylhexenyl group, a cyclopentenyl group, a cyclohexenyl group, and a cycloheptenyl group.

In the present specification, "acyl group" is a general term for an alkylcarbonyl group, an arylcarbonyl group, and a heteroarylcarbonyl group.

In the present specification, "acyloxy group" is a general term for an alkylcarbonyloxy group, an arylcarbonyloxy group, and a heteroarylcarbonyloxy group.

In the present specification, the "aryl group" may be a group composed of only one aromatic hydrocarbon ring or a group obtained by condensing one or more rings to an aromatic hydrocarbon ring. In a case where the aromatic hydrocarbon ring is a group in which one or more rings are condensed, a group in which one or more of an aromatic hydrocarbon ring, an aliphatic hydrocarbon ring, and a non-aromatic heterocyclic ring are condensed to an aromatic hydrocarbon ring can be employed. The carbon number of the aryl group can be, for example, 6 or more and 10 or more. The carbon number can be 30 or less, 18 or less, 14 or less, or 10 or less. Specific examples of aryl groups include a phenyl group, a 1-naphthyl group, and a 2-naphthyl group.

In the present specification, the "heteroaryl group" may be a group composed of only one heteroaromatic ring, or may be a group obtained by condensing one or more rings to a heteroaromatic ring. In a case where the heteroaromatic ring is a group in which one or more rings are condensed, a group in which one or more of an aromatic hydrocarbon ring, a heteroaromatic ring, an aliphatic hydrocarbon ring, and a non-aromatic heterocyclic ring are condensed to an aromatic hydrocarbon ring can be employed. The number of cyclic-skeleton-forming atoms of the heteroaryl group can be, for example, 5 or more, 6 or more, 9 or more, or 10 or more. Furthermore, the number of cyclic-skeleton-forming atoms can be 30 or less, 18 or less, 14 or less, or 11 or less. The heteroaryl group may be a group bonded through a heteroatom or a group bonded through a carbon atom constituting a heteroaromatic ring. Examples of heteroatoms constituting the ring skeleton of the heteroaromatic ring of the heteroaryl group include a nitrogen atom, an oxygen atom, and a sulfur atom. Specific examples of heteroaryl groups include a 2-pyridyl group, a 3-pyridyl group, a 4-pyridyl group, a 2-pyrimidyl group, a 4-pyrimidyl group, a 5-pyrimidyl group, and a triazinyl group.

The "amino group" in the present specification includes a dialkylamino group and a diarylamino group. Two alkyl groups constituting the dialkylamino group may be bonded to each other to form a cyclic structure, and two aryl groups constituting the diarylamino group may be bonded to each other to form a cyclic structure.

The above-described description and specific examples of an alkyl group can be referred to regarding description and specific examples of an alkyl moiety of an "alkoxy group" in the present specification, description and specific examples of an alkyl moiety of an "alkylthio group" in the present specification, description and specific examples of an alkyl moiety (a moiety obtained by removing a carbonyl group from an acyl group) in a case where an "acyl group" in the present specification is an alkylcarbonyl group, description and specific examples of an alkyl moiety (a moiety obtained by removing a carbonyloxy group from an acyl group) in a case where an "acyloxy group" in the present specification is an alkylcarbonyloxy group, description and specific examples of an alkyl moiety (a moiety obtained by removing an oxycarbonyl group from an alkoxycarbonyl group) of an "alkoxycarbonyl group" in the present specification, and each alkyl moiety in a case where an "amino group" in the present specification is a dialkylamino group.

The above-described description and specific examples of an aryl group can be referred to regarding description and specific examples of an aryl moiety (a moiety obtained by removing a carbonyl group from an acyl group) in a case where an "acyl group" in the present specification is an arylcarbonyl group, description and specific examples of an aryl moiety (a moiety obtained by removing a carbonyloxy group from an acyl group) in a case where an "acyloxy group" in the present specification is an arylcarbonyloxy group, description and specific examples of an aryl moiety of an "aryloxy group," description and specific examples of an aryl moiety of an "aryloxycarbonyl group" (a moiety obtained by removing an oxycarbonyl group from an aryloxycarbonyl group), description and specific examples of an aryl moiety of an "arylthio group" in the present specification, and each aryl moiety in a case where an "amino group" in the present specification is a diarylamino group.

The above-described description and specific examples of a heteroaryl group can be referred to regarding description and specific examples of a heteroaryl moiety (a moiety obtained by removing a carbonyl group from an acyl group) in a case where an "acyl group" in the present specification is a heteroarylcarbonyl group, description and specific examples of a heteroaryl moiety (a moiety obtained by removing a carbonyloxy group from an acyl group) in a case where an "acyloxy group" in the present specification is a heteroarylcarbonyloxy group, description and specific examples of a heteroaryl moiety of a "heteroaryloxy group" in the present specification, description and specific examples of a heteroaryl moiety (a moiety obtained by removing an oxycarbonyl group from a heteroaryloxycarbonyl group) of a "heteroaryloxycarbonyl group" in the present specification, and description and specific examples of a heteroaryl moiety of a "heteroarylthio group" in the present specification.

In the present specification, "n-" described before a chain substituent is an abbreviation for normal (linear chain), and "t-" is an abbreviation for tertiary.

In the present specification, a "monomer" is a concept that is distinguished from oligomers and polymers, and refers to a monomer having a weight-average molecular weight of 1,000 or less.

In the present specification, a "refractive index (nd)," an "Abbe number (vd)," and a "partial dispersion ratio (θg, F)" are values measured using a Kalnew precision refractometer (manufactured by Shimadzu Device Manufacturing Co., Ltd., model number KPR-2000). For details of the measurement procedure, the descriptions in Examples 1 to 3 can be referred to. In the present specification, a "refractive index (nd)" is a refractive index at a wavelength of 587.56 nm. Furthermore, an "Abbe number (vd)" and a "partial dispersion ratio (θg, F)" are values calculated from the refractive index measurement values at different wavelengths according to the following equations.

$$vd=(nd-1)/(nF-nC)$$

$$\theta g,F=(ng-nF)/(nF-nC)$$

Where, nd represents a refractive index at a wavelength of 587.56 nm, nF represents a refractive index at a wavelength of 486.13 nm, nC represents a refractive index at a wavelength of 656.27 nm, and ng represents a refractive index at a wavelength of 435.83 nm.

Compound represented by General Formula (1)

(Definition)

The compound represented by General Formula (1) will be described in detail.

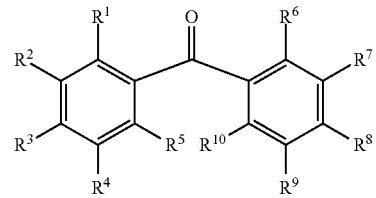

In General Formula (1), $R^1$ to $R^{10}$ each independently represent a hydrogen atom or a substituent. Where, at least one of $R^1, \ldots, R^5$ is an aryl group substituted by a substituent containing a (meth)acryloyloxy group or a heteroaryl group substituted by a substituent containing a (meth)acryloyloxy group. In addition, at least one of $R^6, \ldots,$ or $R^{10}$ is a substituted or unsubstituted aryl group or a substituted or unsubstituted heteroaryl group.

$R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, and $R^9$ and $R^{10}$ each may be bonded to each other to form a linking group necessary to form a cyclic structure. Where, a molecule represented by General Formula (1) does not include a polycyclic structure in which three or more aromatic rings are condensed.

(Description of $R^1$ to $R^5$)

An "aryl group substituted by a substituent containing a (meth)acryloyloxy group" or a "heteroaryl group substituted by a substituent containing a (meth)acryloyloxy group" as at least one of $R^1, \ldots,$ or $R^5$, is an aryl group or a heteroaryl group having at least one substituent containing one or more (meth)acryloyloxy groups. It is preferably an aryl group or heteroaryl group having at least one substituent containing one (meth)acryloyloxy group, is more preferably an aryl group or heteroaryl group having one or two substituents containing one (meth)acryloyloxy group, and is even more preferably an aryl group or heteroaryl group having one substituent containing one (meth)acryloyloxy group. The aryl group or heteroaryl group may have a substituent other than the substituent including the (meth)acryloyloxy group. Preferable examples of such a substituent include a hydroxyl group, an alkyl group, an alkoxy group, and an alkylthio group.

A case in which one or two of $R^1$ to $R^5$ are "an aryl group substituted with a substituent containing a (meth)acryloyloxy group" or "a heteroaryl group substituted with a substituent containing a (meth)acryloyloxy group" is preferable, a case in which one or two of $R^1$ to $R^5$ are "an aryl group substituted with a substituent containing a (meth)acryloyloxy group" is more preferable, and a case in which one of $R^1$ to $R^5$ is "an aryl group substituted with a substituent containing a (meth)acryloyloxy group" is even more preferable.

Among $R^1$ to $R^5$, at least one of $R^2, \ldots,$ or $R^4$ is preferably "an aryl group substituted with a substituent containing a (meth)acryloyloxy group" or "a heteroaryl group substituted with a substituent containing a (meth)acryloyloxy group." At least one of $R^2$ or $R^4$ is particularly preferably "an aryl group substituted by a substituent containing a (meth)acryloyloxy group" or "a heteroaryl group substituted by a substituent containing a (meth)acryloyloxy group" because solubility is further improved.

$R^1$ to $R^5$ other than "an aryl group substituted by a substituent containing a (meth)acryloyloxy group" or "a heteroaryl group substituted by a substituent containing a (meth)acryloyloxy group" are a substituent other than these groups or a hydrogen atom. Among $R^1$ to $R^5$, the number of substituents other than these is preferably 0 to 2, and it may be 0 or 1, for example.

(Description of $R^6R^{10}$)

An "aryl group" as $R^6$ to $R^{10}$ may be an aryl group substituted by a substituent containing a (meth)acryloyloxy group. In that case, the group may be the same as or different from the "aryl group substituted by a substituent containing a (meth)acryloyloxy group" represented by any of $R^1$ to $R^5$. A case in which they are the same group is preferable.

In addition, a "heteroaryl group" as $R^6$ to $R^{10}$ may be a heteroaryl group substituted by a substituent containing a (meth)acryloyloxy group. In that case, the group may be the same as or different from the "heteroaryl group substituted by a substituent containing a (meth)acryloyloxy group" represented by any of $R^1$ to $R^5$. A case in which they are the same group is preferable.

Among $R^6$ to $R^{10}$, it is preferable that at least one of $R^7, \ldots,$ or $R^9$ is an aryl group, and examples include a case in which at least one of $R^7, \ldots,$ or $R^9$ is an aryl group, and a case in which $R^8$ is an aryl group. A case where at least one of $R^7, \ldots,$ or $R^9$ is an aryl group is preferable because solubility further tends to be improved.

(Substituent Containing (Meth)Acryloyloxy Group)

It is sufficient that a "substituent containing a (meth)acryloyloxy group" in an "aryl group substituted with a substituent containing a (meth)acryloyloxy group" or a "heteroaryl group substituted with a substituent containing a (meth)acryloyloxy group" as $R^1$ to $R^{10}$ is any substituent containing a (meth)acryloyloxy group, but a group represented by General Formula (4) is particularly preferable.

$$Ac(-L^1-L^2)_{m1}(-L^3)_{m2}-* \quad \text{General Formula (4)}$$

In General Formula (4),

Ac represents a (meth)acryloyloxy group, $L^1$ represents an alkylene group that has 1 to 6 carbon atoms and may have a substituent, $L^2$ represents a carbonyl group, an ether group, a thiocarbonyl group, a thioether group, or a linking group that is a combination of these groups, $L^3$ represents an alkylene group that has 1 to 6 carbon atoms and may have a substituent, m1 represents any integer of 0 to 10, in which in a case where m1 is 2 or more, a plurality of $L^1$'s may be the same as or different from each other, and a plurality of $L^2$'s may be the same as or different from each other, m2 represents 0 or 1, and

* represents a binding site of a substituent containing a (meth)acryloyloxy group.

The carbon number of the alkylene group as $L^1$ in General Formula (4) is preferably 2 to 6, and more preferably 2 to 5. Examples thereof include an ethylene group, a 1-methylethylene group, a 2-methylethylene group, an n-propylene group, a 2-methylpropylene group, a 2,2-dimethylpropylene group, and a n-butylene group. The alkylene group is described with the atom on the side bonded to $L^2$ as the position 1. A case where $L^1$ is a branched alkylene group is preferable because solubility is further improved.

m1 is preferably 1 to 5, more preferably 1 to 3, and may be 1 or 2. In a case where m is 2 or more, a plurality of $L^1$'s may be the same as or different from each other, but they are preferably the same. A plurality of $L^2$'s may be the same as or different from each other, but they are preferably the same.

The carbon number of the alkylene group as $L^3$ in General Formula (4) is preferably 1 to 6, and more preferably 1 to 3. Examples thereof include a methylene group, an ethylene group, a 1-methylethylene group, a 2-methylethylene group, and an n-propylene group. An alkylene group is described with the atom bonded to $L^3$ or the *-marked atom in General Formula (4) as the position 1.

m2 may be either 0 or 1, but in a case where it is 1, the alkylene groups represented by $L^1$ and $L^3$ may be the same as or different from each other.

Specific examples of the linking group as $L^2$ in General Formula (4) include the following. The  mark on the left side of each linking group indicates the binding position to $L^1$. In a case where m2 is 1, the  mark on the right side indicates the binding position to $L^3$, and in a case where m2 is 0, it is synonymous with the mark * in General Formula (4).

In a case where m is 2 or more, the plurality of $L^2$'s may be the same as or different from each other.

—CO—
—O—
—CS—
—S—
—CO—O—
—O—CO—
—CO—S—
—S—CO—
—CS—O—
—O—CS—
—CS—S—
—S—CS—

Examples of substituents containing a (meth)acryloyloxy group include a (meth)acryloyloxyalkoxy group, a (meth)acryloyloxyalkoxyalkyl group, a (meth)acryloyloxyalkoxycarbonylalkyl group, a (meth)acryloyloxyalkoxycarbonylacyloxy group, or a (meth)acryloyloxyalkoxycarbonylacyloxyalkyl group.

The chain length of a "substituent containing a (meth)acryloyloxy group" is preferably 7 to 20, and more preferably 8 to 15. By increasing the chain length to a preferred range, solubility of the compound can be improved.

The position at which the "substituent containing a (meth)acryloyloxy group" is bonded to the aryl group or heteroaryl group may be any position of these aryl groups or heteroaryl groups, but is preferably any one or more of the positions 3 to 5. An atom in which the "aryl group substituted by a substituent containing a (meth)acryloyloxy group" or the "heteroaryl group substituted by a substituent containing a (meth)acryloyloxy group" is bonded to benzophenone is described as an atom at the position 1.

The number of "substituents containing a (meth)acryloyloxy group" in the compound represented by General Formula (1) is preferably 2 or more, more preferably 2 to 4, and even more preferably 2 or 3.

Specific examples of "substituents containing a (meth)acryloyloxy group" will be described later. However, the "substituent containing a (meth)acryloyloxy group" that can be employed in the present invention is not limitedly interpreted by these specific examples. In the following structure, R represents a hydrogen atom or a methyl group, and * represents a binding position to an aryl group or a heteroaryl group.

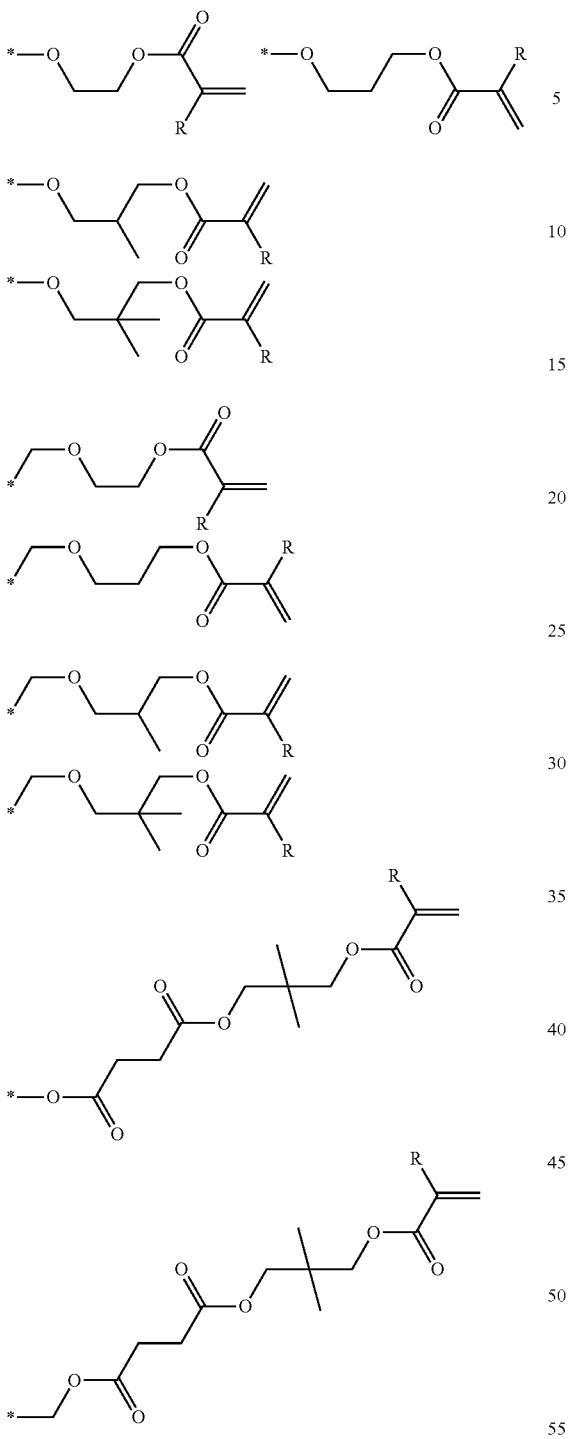

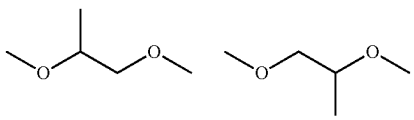

The following notation in the present application indicates one of the following structures.

That is, it shows a structure in which a methyl group is bonded to any one carbon atom constituting the oxyethyleneoxy group.

(Substituent Not Containing (Meth)Acryloyloxy Group)

$R^1$ to $R^{10}$ may be a substituent that is not an "aryl group substituted by a substituent containing a (meth)acryloyloxy group" or a "heteroaryl group substituted by a substituent containing a (meth)acryloyloxy group" described above. Examples of such a substituent include a substituent not containing a (meth)acryloyloxy group. In addition, preferable examples of such a substituent include a hydroxyl group, an alkyl group, an alkoxy group, and an alkylthio group. Prescribing from another viewpoint, an alkyl group or a group represented by General formula (5) can be mentioned as a preferable substituent.

$$T(-L^1-L^2)_{m1}(-L^3)_{m2}-* \qquad \text{General Formula (5)}$$

In General Formula (5),

T represents a hydrogen atom, a hydroxyl group, or a halogen atom, $L^1$ represents an alkylene group that has 1 to 6 carbon atoms and may have a substituent, $L^2$ represents a carbonyl group, an ether group, a thiocarbonyl group, a thioether group, or a linking group that is a combination of these groups, $L^3$ represents an alkylene group that has 1 to 6 carbon atoms and may have a substituent, m1 represents any integer of 0 to 10, in which in a case where m1 is 2 or more, a plurality of $L^1$'s may be the same as or different from each other, and a plurality of $L^2$'s may be the same as or different from each other, m2 represents 0 or 1, and in a case where T is a hydrogen atom and m1 is 0, m2 is 1, and

* represents a binding site of the substituent represented by General Formula (5).

For the description and specific examples of $L^1$, $L^2$, $L^3$, m1, and m2 in General Formula (5), the corresponding description in General Formula (4) can be referred to.

Specific examples of the group represented by General Formula (5) include the following groups. However, groups that can be employed in the present invention are not limitedly interpreted by the following specific examples.

HO—*
$CH_3O$—*
$CH_3CH_2O$—*
$HOCH_2CH_2O$—*
$CH_3OCH_2CH_2O$—*
$CH_3S$—*
$CH_3CH_2S$—*

(Formation of Cyclic Structure)

$R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, and $R^9$ and $R^{10}$ in General Formula (1) each may be bonded to each other to form a linking group necessary to form a cyclic structure. The formed cyclic structure may be an aromatic ring or a non-aromatic ring. In addition, the formed cyclic structure may be a cyclic structure in which the cyclic-skeleton-forming atoms are composed of only carbon atoms, or may be a cyclic structure including a heteroatom as the cyclic-skeleton-forming atoms. A cyclic structure in which the cyclic-skeleton-forming atoms consist only of carbon atoms is preferable. Examples of cyclic structures formed include a benzene ring, a pyridine ring, a pyrimidine ring, and a cyclohexene ring. These rings may be substituted by a substituent. Where, a molecule represented by General Formula (1) does not include a polycyclic structure in which three or more aromatic rings are condensed.

Furthermore, a case in which any two of $R^1$ to $R^{10}$ are not bonded to each other to form a cyclic structure is preferable.

(Conjugated System)

The compound represented by General Formula (1) has a conjugated system containing a benzophenone structure. The number of atoms constituting one conjugated system containing a benzophenone structure (the number of conjugated atoms having conjugated π electrons) is preferably 24 to 38, more preferably 24 to 34, even more preferably 26 to 34, and further more preferably 26 to 32. By appropriately controlling the number of atoms constituting one conjugated system containing a benzophenone structure, it is possible to avoid a decrease in solubility and coloring of the compound. Among the atoms constituting one conjugated system containing a benzophenone structure, 1 to 7 heteroatoms are preferably contained, 1 to 5 atoms are more preferably contained, and 1 to 3 atoms can be contained for example.

(Symmetry)

The compound represented by General Formula (1) may be a symmetrical compound in which the groups bonded to the left and right of the carbonyl group described in the center of General Formula (1) are the same, or may be an asymmetric compounds in which the groups bonded to the left and right are different groups. In a case where it is a symmetrical compound, there is an advantage that a synthesis is easy.

Compound represented by General Formula (2)

(Definition)

The compound represented by General Formula (1) is preferably a compound represented by General Formula (2).

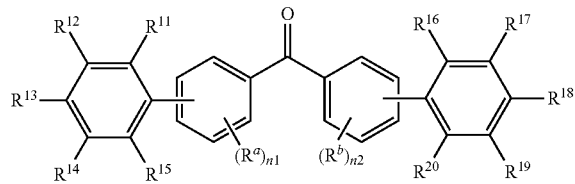

General Formula (2)

In General Formula (2), $R^a$ and $R^b$ each independently represent a substituent other than an aryl group and a heteroaryl group, n1 and n2 each independently represent an integer of 0 to 4, in which in a case where n1 is 2 or more, a plurality of $R^a$'s may be the same as or different from each other, and in a case where n2 is 2 or more, a plurality of $R^b$'s may be the same as or different from each other, $R^{11}$ to $R^{20}$ each independently represent a hydrogen atom or a substituent, and at least one of $R^{11}, \ldots,$ or $R^{15}$ is a substituent containing a (meth)acryloyloxy group.

$R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, and $R^{19}$ and $R^{20}$; two $R^a$'s respectively bonded to adjacent cyclic-skeleton-forming atoms of a benzene ring; and two $R^b$'s respectively bonded to adjacent cyclic-skeleton-forming atoms of a benzene ring each may be bonded to each other to form a linking group necessary to form a cyclic structure. Where, a molecule represented by General Formula (2) does not include a polycyclic structure in which three or more aromatic rings are condensed.

(Substituent of Benzophenone)

The compound represented by General Formula (2) is a compound having a structure in which one substituted phenyl group is substituted on each benzene ring of benzophenone. The substitution position of the substituted phenyl group may be any position on the benzene ring of benzophenone. Each benzene ring of benzophenone may be substituted by $R^a$ and $R^b$ which are substituents other than the aryl group and heteroaryl group. The number of substitutions n1 of $R^a$ and the number of substitutions n2 of $R^b$ are preferably each independently 0 to 2, and may be 0 or 1. The substitution position of the substituted phenyl group on each benzene ring of benzophenone is preferably any one of the positions 3 to 5, or positions 3' to 5', but the substitution positions of $R^a$ and $R^b$ may be any one of positions 2 to 6 or positions 2' to 6'.

(Description of $R^a$ and $R^b$)

$R^a$ and $R^b$ are not particularly limited as long as they are substituents other than an aryl group and a heteroaryl group, but preferable examples thereof include a hydroxyl group, an alkyl group, an alkoxy group, and an alkylthio group, and more preferable examples thereof include an alkyl group and an alkoxy group. Specific examples of substituents as $R^a$ and $R^b$ include the groups listed as specific examples of the group represented by General Formula (5).

(Description of $R^{11}$ to $R^{15}$)

At least one of $R^{11}, \ldots,$ or $R^{15}$ is a "substituent containing a (meth)acryloyloxy group." The "substituent containing a (meth)acryloyloxy group" is preferably any one or more of $R^{12}$ to $R^{14}$. A case where it is $R^{12}$ is preferable from the viewpoint that solubility becomes favorable. The remaining $R^{11}$ to $R^{15}$ other than a "substituent containing (meth)acryloyloxy group" are substituents other than "substituents containing (meth)acryloyloxy group" or a hydrogen atom. Among $R^{11}$ to $R^{15}$, the number of substituents other than "substituents containing a (meth)acryloyloxy group" is preferably 0 to 2, and may be 0 or 1. Specific examples of substituents preferably include a hydroxyl group, an alkyl group, an alkoxy group, and an alkylthio group, and these groups are also preferably substituted by an alkoxy group, an alkoxyalkyleneoxy group, or a group having an alkyleneoxy repeating unit. Among $R^{11}$ to $R^{15}$, $R^{11}$ and $R^{15}$ are preferably hydrogen atoms.

(Description of $R^{16}$ to $R^{20}$)

$R^{16}$ to $R^{20}$ each independently represent a hydrogen atom or a substituent. At least one of $R^{16}, \ldots,$ or $R^{20}$ is preferably a substituent, and the substituent is preferably a "substituent containing a (meth)acryloyloxy group", and at least one of them is preferably a "substituent containing (meth)acryloyloxy group." The "substituent containing (meth)acryloyloxy group" represented by at least one of $R^{16}, \ldots,$ or $R^{20}$ and the "substituent containing (meth)acryloyloxy group" represented by at least one of $R^{11}, \ldots,$ or $R^{15}$ may the same as or different from each other, however, they are preferably the same. The number of substituents other than "substituents containing a (meth)acryloyloxy group" as $R^{16}$ to $R^{20}$ is preferably 0 to 2, and may be 0 or 1, for example. The carbon number of substituents other than "substituents containing a (meth)acryloyloxy group" is preferably 1 to 10. Specific examples of substituents preferably include a hydroxyl group, an alkyl group, an alkoxy group, and an alkylthio group, and these groups are also preferably substituted by an alkoxy group, an alkoxyalkyleneoxy group, or a group having an alkyleneoxy repeating unit. Among $R^{16}$ to $R^{20}$, $R^{16}$ and $R^{20}$ are preferably hydrogen atoms.

For the description and specific examples of "substituents containing a (meth)acryloyloxy group" as $R^{11}$ to $R^{20}$, and the description and specific examples of the cyclic structure formed by bonding of $R^{11}$ and $R^{12}$ and the like with each other, the corresponding description in the description of General Formula (1) can be referred to.

Compound Represented by General Formula (3)
(Definition)

The compound represented by General Formula (1) includes a compound represented by General Formula (3).

General Formula (3)

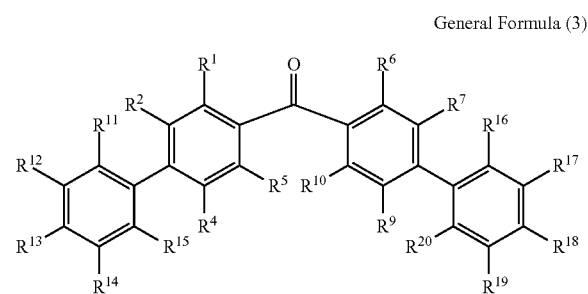

In General Formula (3),
$R^1$, $R^2$, $R^4$, $R^5$, $R^6$, $R^7$, $R^9$, and $R^{10}$ each independently represent a hydrogen atom or a substituent other than an aryl group and a heteroaryl group,
$R^{11}$ to $R^{20}$ each independently represent a hydrogen atom or a substituent, and
at least one of $R^{11}, \ldots,$ or $R^{15}$ is a substituent containing a (meth)acryloyloxy group.

$R^1$ and $R^2$, $R^4$ and $R^5$, $R^6$ and $R^7$, $R^9$ and $R^{10}$, $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, and $R^{19}$ and $R^{20}$ each may be bonded to each other to form a linking group necessary to form a cyclic structure. Where, a molecule represented by General Formula (3) does not include a polycyclic structure in which three or more aromatic rings are condensed.

(Description)

The compound represented by General Formula (3) is a compound having a structure in which a substituted phenyl group is substituted at the position 4 and position 4' of benzophenone. For descriptions and specific examples of $R^1$, $R^2$, $R^4$, $R^5$, $R^6$, $R^7$, $R^9$, and $R^{10}$ in General Formula (3), reference can be made to the descriptions and specific examples of $R^a$ and $R^b$ in General Formula (2). For the description and specific examples of $R^{11}$ to $R^{20}$ in General Formula (3), the corresponding description in General Formula (2) can be referred to. For the description and specific examples of the cyclic structure that can be formed by bonding of $R^1$ and $R^2$ and the like with each other, the corresponding description in General Formula (1) can be referred to.

SPECIFIC EXAMPLES

Specific examples of the compound represented by General Formula (1) will be described below. However, the compound represented by General Formula (1) that can be employed in the present invention is not limitedly interpreted by these specific examples. Me represents a methyl group.

A-1

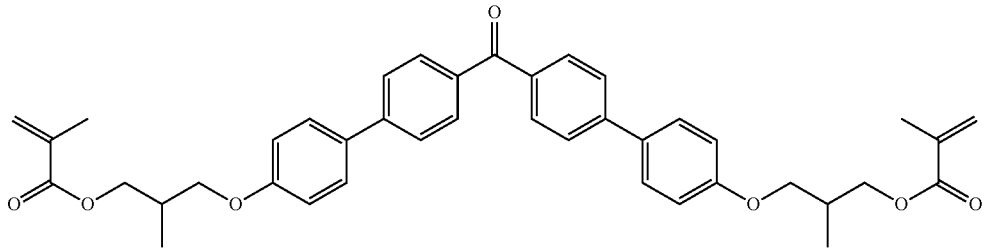

A-2

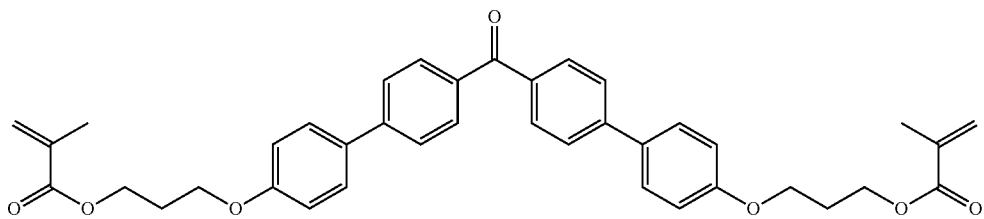

A-3

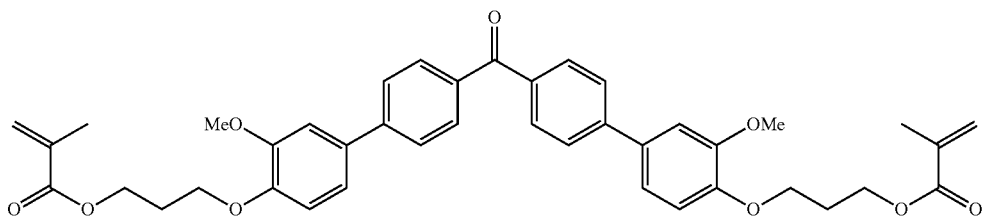

-continued
A-4
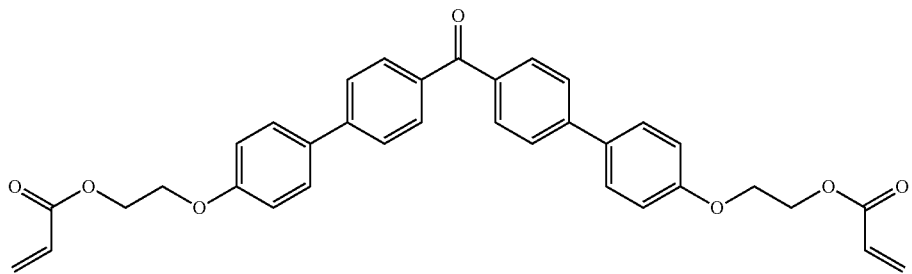
A-5
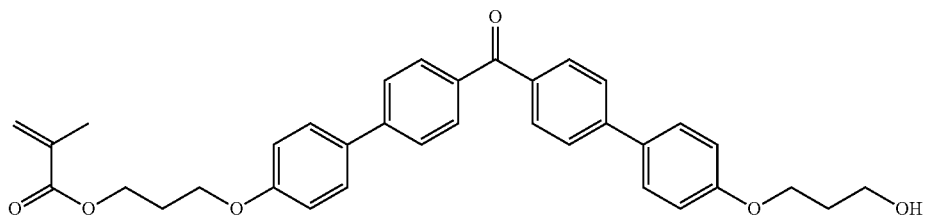
A-6
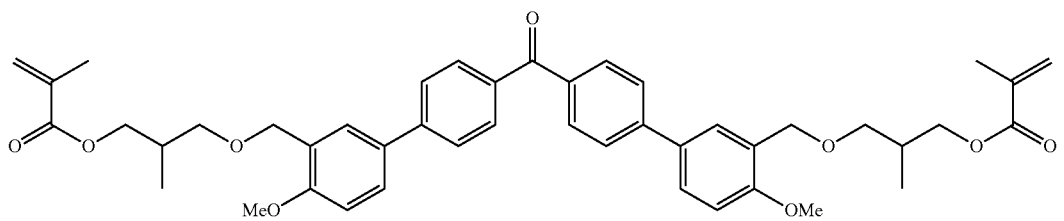
A-7
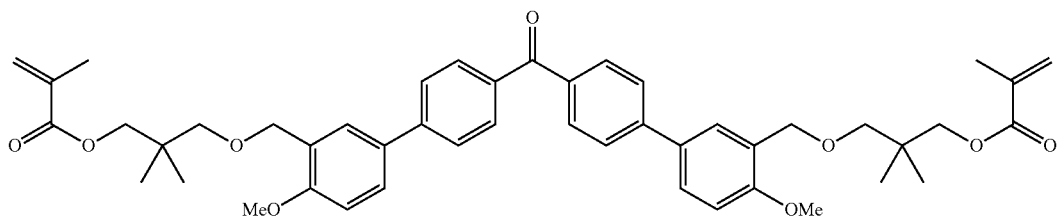
A-8
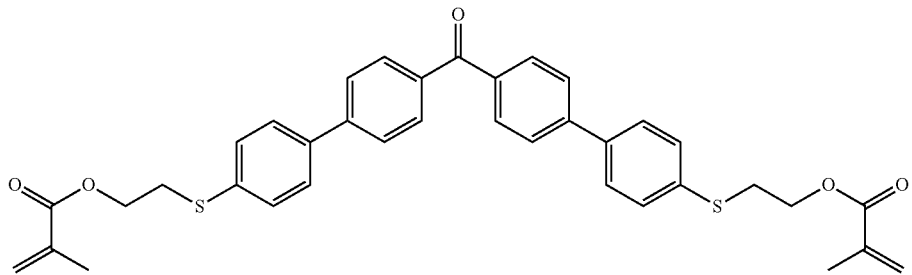
A-9
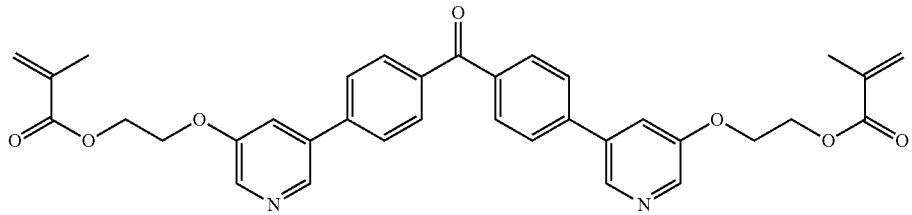

-continued
A-10
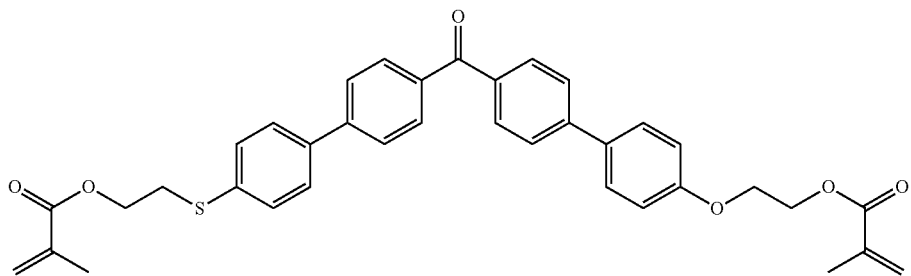
A-11
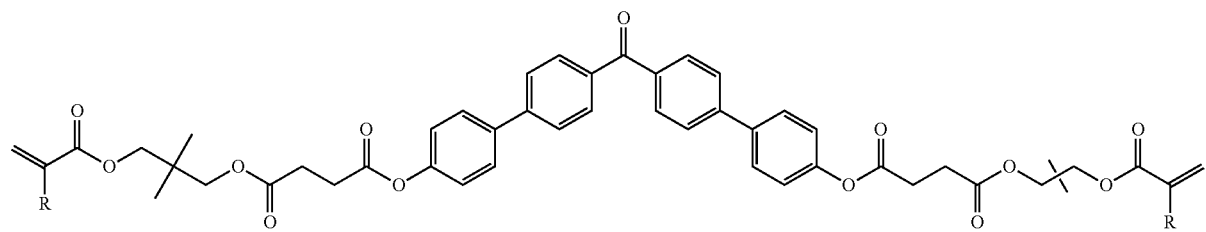
A-12
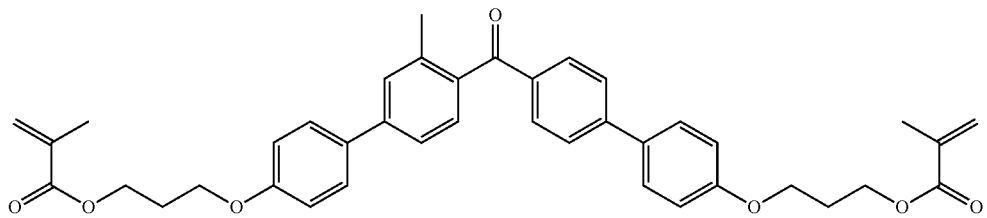
A-13
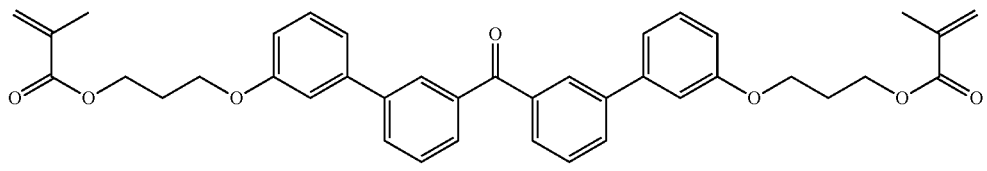
A-14
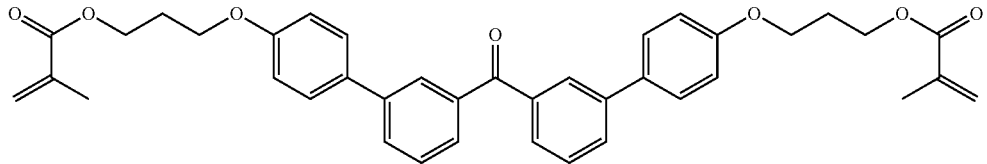
A-15
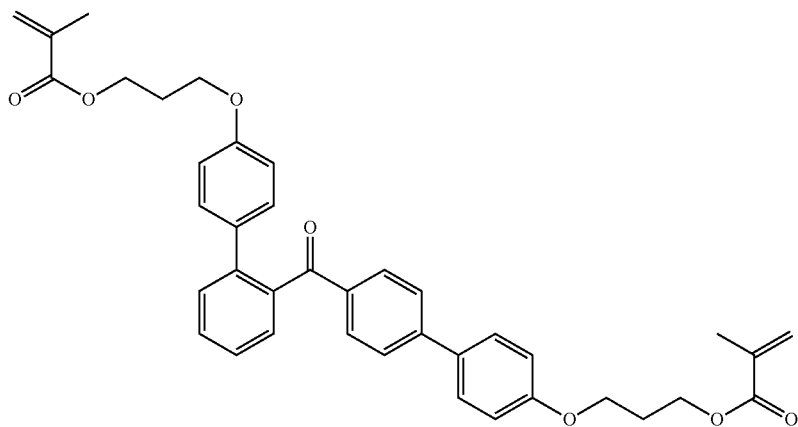

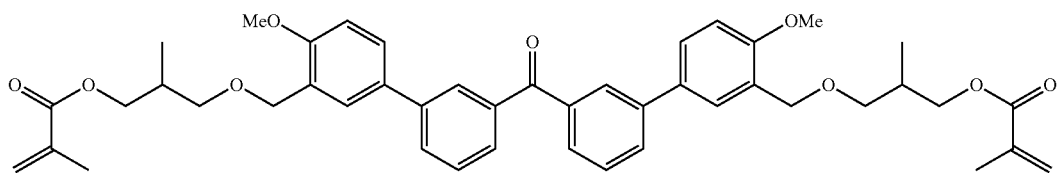

A-16

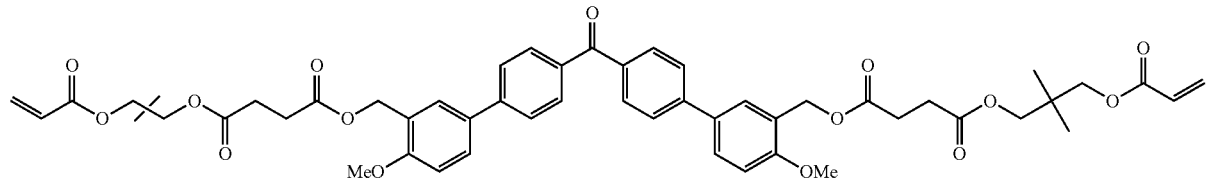

A-17

Synthesis Method

The compound represented by General Formula (1) can be synthesized by appropriately combining known synthesis methods.

For example, benzophenone substituted with a halogen atom at the position where the substituent is to be introduced is selected as a starting material, and reacting with hydroxyphenylboronic acid, and thereby a compound in which a halogen atom is substituted with a hydroxyphenyl group can be synthesized. Next, the hydroxyl group of the synthesized compound is reacted with a hydroxyalkyl halide to convert the hydroxyl group to a hydroxyalkoxy group, and further reacted with an acryloyl halide, thereby a compound represented by General Formula (1) having an acryloyl group introduced at the terminal can be synthesized. Each of these steps is a well-known synthesis reaction, and the reaction conditions and the like can be appropriately adjusted and optimized within a generally known range.

For specific synthesis procedures of the compound represented by General Formula (1), Examples 1 to 3 to be described later can be referred to.

Characteristics of Compounds

The compound represented by General Formula (1) exhibits excellent refractive index characteristics without being cured. That is, the compound represented by General Formula (1) exhibits a high refractive index (nd), a low Abbe number (vd), and a high partial dispersion ratio (θg, F), and is a compound that can be used for optical members without curing.

The Abbe number (vd) of the compound represented by General Formula (1) is not particularly limited, but the Abbe number of the film formed by coating the compound dissolved in a suitable solvent such as propylene glycol monomethyl ether acetate is preferably 25 or less, more preferably 20 or less, even more preferably 19 or less, and particularly preferably 18 or less. By keeping the Abbe number (vd) low, chromatic aberration can be corrected over a wide wavelength range.

In addition, the partial dispersion ratio (θg, F) of the compound represented by General Formula (1) is not particularly limited, but the partial dispersion ratio (θg, F) of the film formed by dissolving the compound in a suitable solvent is preferably 0.70 or more, more preferably 0.73 or more, and even more preferably 0.77 or more. By increasing the partial dispersion ratio (θg, F), it is possible to effectively correct chromatic aberration particularly at a short wavelength.

In a case where the compound represented by General Formula (1) is used as a compound for an optical member without being cured, it can be used by dispersing the compound in a matrix polymer. As the matrix polymer, a material described in paragraph 0098 of JP2012-167019A cited herein as a part of the present specification can be used. These materials may be used alone or in combination of two or more kinds thereof. In a case of selecting a matrix polymer, it is preferable to select in consideration of compatibility with the compound represented by General Formula (1). In a case where compound is dispersed in the matrix polymer, the content of the compound is preferably 1% to 70% by mass, and more preferably 5% to 50% by mass.

Curable Composition

By curing the compound represented by General Formula (1), it is possible to form a cured product having excellent refractive index characteristics and excellent moisture-heat stability. In the case of curing, it is preferable to prepare a curable composition containing the compound represented by General Formula (1) and cure it.

The content of the compound represented by General Formula (1) in the curable composition is preferably 1% to 99% by mass, is more preferably 10% to 90% by mass, and is even more preferably 20% to 80% by mass with respect to the total mass of the curable composition.

The curable composition can contain various components in addition to the compound represented by General Formula (1). For example, a (meth)acrylate monomer other than the compound represented by General Formula (1), a polymerization control agent, and a polymerization initiator can be preferably contained. As the polymerization initiator, it is preferable to use at least one selected from a photoradical polymerization initiator or a thermal radical polymerization initiator. The curable composition can also contain a polymer having a radically polymerizable group in the side chain. These components will be described in detail below.

((Meth)Acrylate Monomer)

The (meth)acrylate monomer that can be used in the curable composition of the embodiment of the present invention may be a polyfunctional (meth)acrylate monomer having two or more (meth)acryloyl groups in the molecule, and may be a monofunctional (meth)acrylate monomer having one (meth)acryloyl group in the molecule.

Specific examples of (meth)acrylate monomers include the (meth)acrylate monomers described in paragraphs 0037 to 0046 of JP2012-107191A, which are incorporated herein as part of the present specification.

Examples of (meth)acrylate monomers that can be preferably used in the present invention include a monofunctional (meth)acrylate monomer having an aromatic ring represented by a monomer 1 (phenoxyethyl acrylate) or a monomer 2 (benzyl acrylate), a bifunctional (meth)acrylate monomer having an aliphatic ring represented by a monomer 3 (tricyclodecane dimethanol diacrylate), and a monofunctional (meth)acrylate monomer having an aliphatic ring represented by a monomer 4 (dicyclopentanyl acrylate). A molecular weight of the (meth)acrylate monomer is preferably 100 to 500.

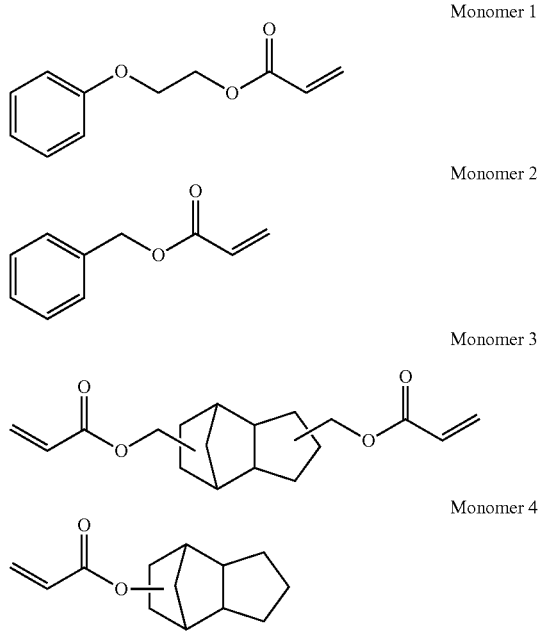

The method of obtaining the (meth)acrylate monomer is not particularly limited, and the compound may be commercially available or may be manufactured by synthesis. In a case of commercially obtaining the compound, for example, VISCOAT #192 PEA (Monomer 1) (manufactured by Osaka Organic Chemical Industry Ltd.), VISCOAT #160 BZA (Monomer 2) (manufactured by Osaka Organic Chemical Industry Ltd.), A-DCP (Monomer 3) (manufactured by Shin-Nakamura Chemical Co., Ltd.), or FA-513AS (Monomer 4) (manufactured by Hitachi Chemical Co., Ltd.) may be preferably used.

When the curable composition of the embodiment of the present invention contains a (meth)acrylate monomer, the content of the (meth)acrylate monomer is preferably 1% to 80% by mass, more preferably 2% to 50% by mass, and still more preferably 3% to 40% by mass, with respect to the total mass of the curable composition.

(Polymerization Control Agent)

In the curable composition of the embodiment of the present invention, a compound having a function of controlling the polymerization of the polymerizable component of the curable composition can be used as a polymerization control agent. As a preferred polymerization control agent, for example, a non-conjugated vinylidene group-containing compound can be employed. As the non-conjugated vinylidene group-containing compound, compounds described in paragraphs 0016 to 0033 of JP2012-107191A cited herein as a part of the present specification can be used.

The molecular weight of the non-conjugated vinylidene group-containing compound is preferably 100 to 400, more preferably 120 to 350, and particularly preferably 130 to 300. The method of obtaining the non-conjugated vinylidene group-containing compound is not particularly limited, and the compound may be commercially available or may be manufactured by synthesis. In a case of commercially obtaining the compound, for example, β-caryophyllene (manufactured by Inoue Perfumery Co., Ltd.) and (+)-limonene (manufactured by Tokyo Chemical Industry Co., Ltd.) can be preferably used.

When the curable composition of the embodiment of the present invention contains a non-conjugated vinylidene group-containing compound, a content of the non-conjugated vinylidene group-containing compound is preferably 0.5% to 30% by mass, more preferably 1% to 25% by mass, and still more preferably 2% to 20% by mass, with respect to the total mass of the curable composition.

(Thermal Radical Polymerization Initiator)

Examples of thermal radical polymerization initiators that can be used in the curable composition of the embodiment of the present invention include 1,1-di(t-hexylperoxy)cyclohexane, 1,1-di(t-butylperoxy)cyclohexane, 2,2-di(4,4-di-(t-butylperoxy)cyclohexyl)propane, t-hexylperoxyisopropyl monocarbonate, t-butylperoxy-3,5,5-trimethylhexanoate, t-butylperoxy laurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, t-butylperoxy-2-ethylhexyl, 2,3-dimethyl-2,3-diphenylbutane, and the like.

Among them, it is preferable that the curable composition of the embodiment of the present invention contains a hydroperoxide compound as a thermal radical polymerization initiator. The hydroperoxide compound is a peroxide and a compound having a peroxy group. In the hydroperoxide compound, one oxygen atom of the peroxy group (—O—O—) is substituted by a hydrogen atom and includes a hydroperoxide group (—O—O—H). Hydroperoxide compounds having hydroperoxide groups in the molecule have the effect of promoting chain transfer during the polymerization of non-conjugated vinylidene group-containing compounds, and the controllability of the three-dimensional structure when the curable composition is cured is more improved, and thereby it is possible to improve and impart deformability to the semi-cured product.

The method of obtaining the hydroperoxide compound is not particularly limited, and the compound may be commercially available or may be manufactured by synthesis. When commercially obtained, for example, PERCUMYL H-80 (cumene hydroperoxide) manufactured by Nippon Oil & Fats Co., Ltd. can be used.

The thermal radical polymerization initiator preferably includes a hydroperoxide compound and another thermal radical polymerization initiator. Examples of other thermal radical polymerization initiators include non-hydroperoxide compounds. Since the hydroperoxide compound generally has a high temperature for initiating thermal radical polymerization, it preferably contains both non-hydroperoxide compounds having a low thermal polymerization initiation temperature. As non-hydroperoxide compounds, it is preferable to use a peroxyester compound such as t-butylperoxy-2-ethylhexanoate (Perbutyl O, manufactured by Nippon Yushi Co., Ltd.,), and t-butylperoxy-2-ethylhexyl carbonate (Perbutyl E, manufactured by Nippon Yushi Co., Ltd.).

The content of the thermal radical polymerization initiator is preferably 0.01% to 10% by mass, more preferably 0.05% to 5.0% by mass, and still more preferably 0.05% to 2.0% by mass, with respect to the total mass of the curable composition.

It is possible to mold a cured product having high heat resistance by thermally polymerizing the curable composition containing the thermal radical polymerization initiator.

(Photoradical Polymerization Initiator)

Examples of photoradical polymerization initiators that can be used in the curable composition of the embodiment of the present invention include bis(2,6-dimethoxybenzoyl)-2,4,4-trimethylpentylphosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)butanone-1,2,4,6-trimethylbenzoyl-diphenyl-phosphine oxide, bis(2,4,6-trimethylbenzoyl)-phenylphosphine oxide, and the like.

Of the above, in the present invention, BASF's IRGACURE 184 (1-hydroxycyclohexyl phenyl ketone), IRGACURE 819 (bis(2,4,6-trimethylbenzoyl)-phenylphosphine oxide), IRGACURE 651 (2,2-dimethoxy-1,2-diphenylethane-1-one), 1-[4-(2-hydroxyethoxy)-phenyl]-2-hydroxy-2-methyl-1-propan-1-one, or 2-methyl-1-(4-methylthiophenyl)-2-morpholinopropan-1-one may be preferably used as the photoradical polymerization initiator.

The content of the photoradical polymerization initiator is preferably 0.01% to 5.0% by mass, more preferably 0.05% to 1.0% by mass, and still more preferably 0.05% to 0.5% by mass, with respect to the total mass of the curable composition.

The curable composition preferably contains both a photoradical polymerization initiator and a thermal radical polymerization initiator described above, and in this case, the total content of a photoradical polymerization initiator and a thermal radical polymerization initiator is preferably 0.01% to 10% by mass, more preferably 0.05% to 5.0% by mass, and still more preferably 0.05% to 3.0% by mass, with respect to the total mass of the curable composition.

(PolymeR Having Radically Polymerizable Group in Side Chain)

A polymer having a radically polymerizable group in the side chain functions to increase the viscosity of the curable composition, and thus functions as a thickener or a thickening polymer. For this reason, it is possible to adjust the viscosity of the curable composition within a desired range by adding an appropriate amount of a polymer having a radically polymerizable group in the side chain to the curable composition.

The polymer having a radically polymerizable group in the side chain may be a homopolymer or a copolymer. Among them, it is preferable that the polymer which has a radically polymerizable group in a side chain be a copolymer. When the polymer having a radically polymerizable group in the side chain is a copolymer, it is sufficient that at least one copolymer component has a radically polymerizable group. In addition, in a case where the polymer having a radically polymerizable group in the side chain is a copolymer, the thickening polymer is more preferably a copolymer containing a monomer unit having a radically polymerizable group in the side chain and a monomer unit having an aryl group in the side chain.

Examples of radically polymerizable groups include a (meth)acrylate group, a vinyl group, a styryl group, and an allyl group. The polymer having a radically polymerizable group in the side chain preferably contains 5% to 100% by mass, more preferably 10% to 90% by mass, and even more preferably 20% to 80% by mass of repeating units having a radically polymerizable group.

In the following, specific examples of the polymer having a radically polymerizable group in the side chain preferably used in the present invention are exemplified, but the polymer having a radically polymerizable group in the side chain is not limited to the following structure.

In the structural formulas below, Ra and Rb each independently represent hydrogen or a methyl group. Note that a plurality of Ra's in one polymer may be the same or different. n represents an integer of 0 to 10, preferably 0 to 2, and more preferably 0 or 1.

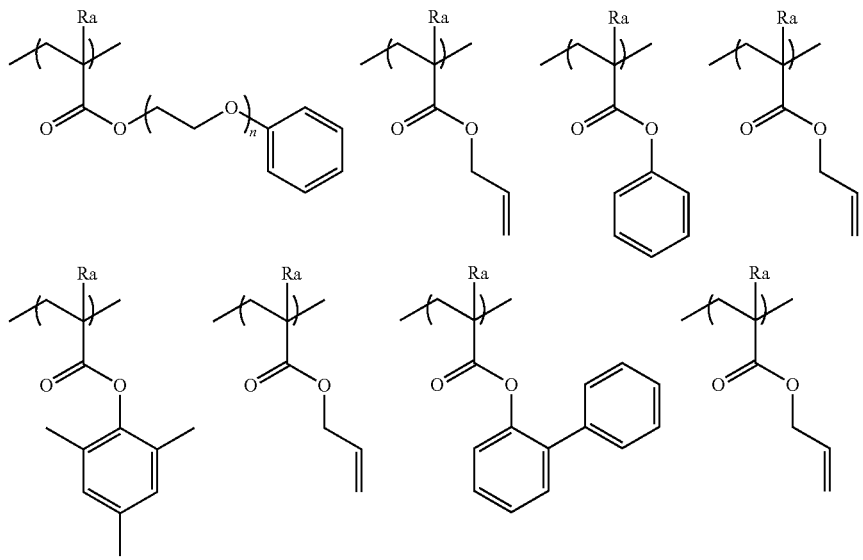

-continued
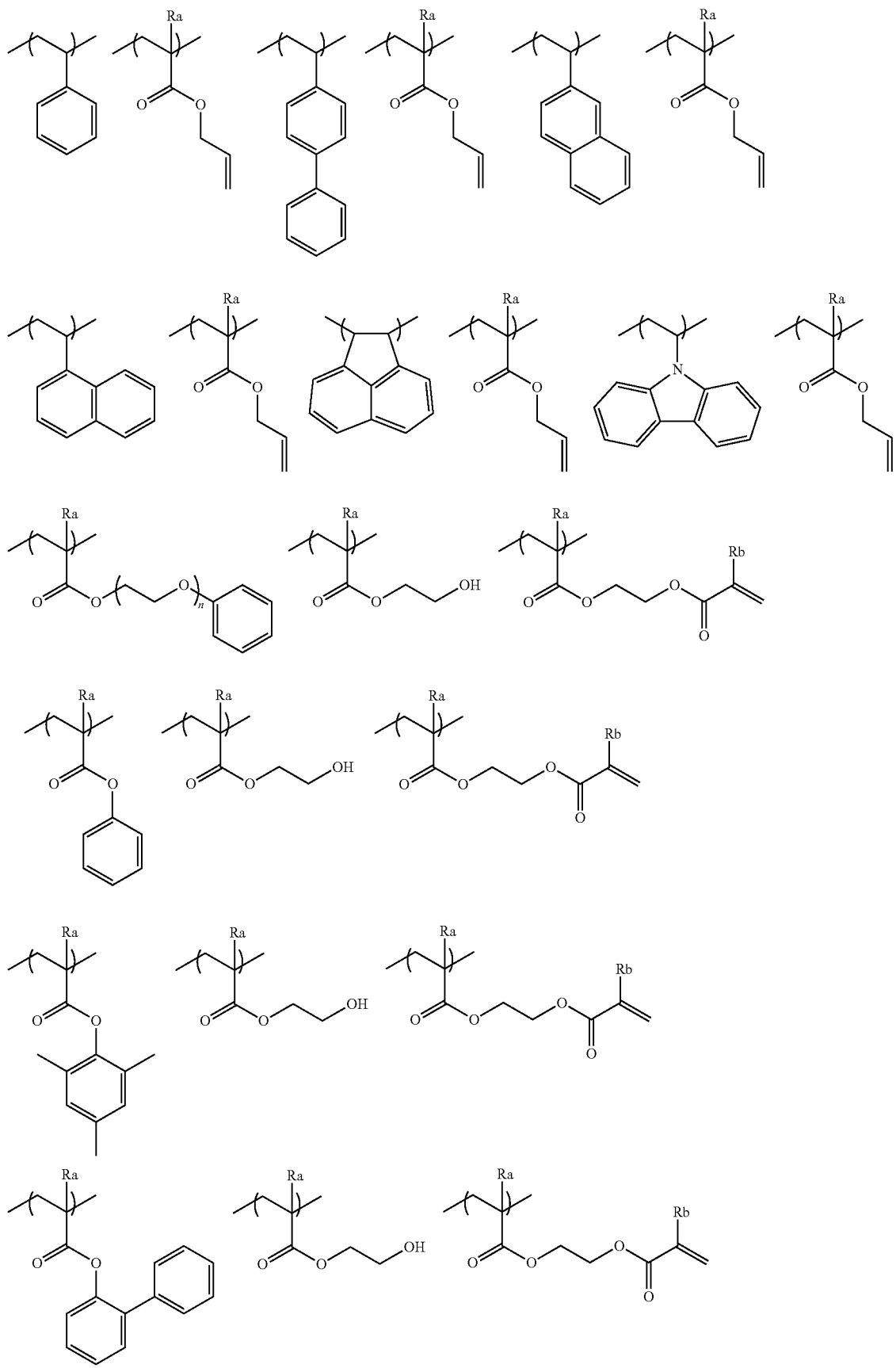

-continued
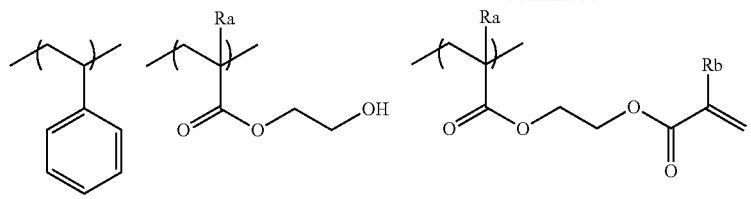
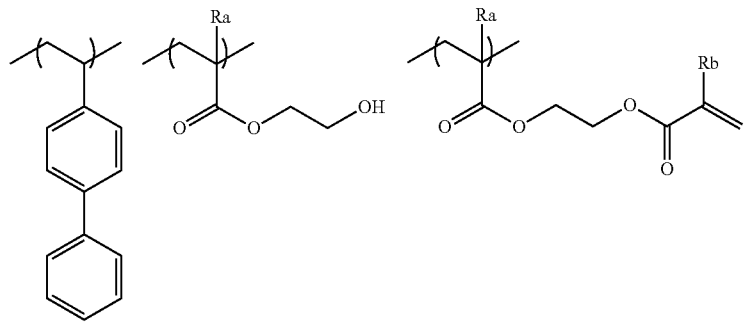
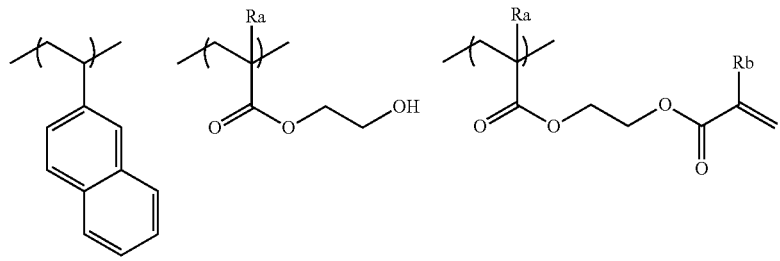
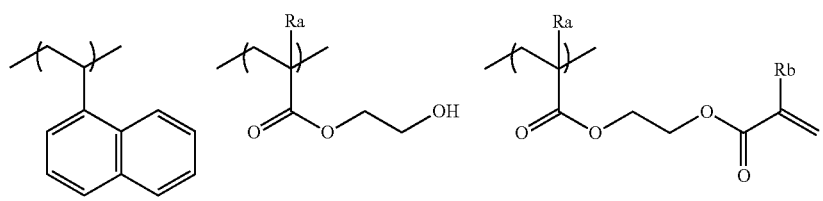
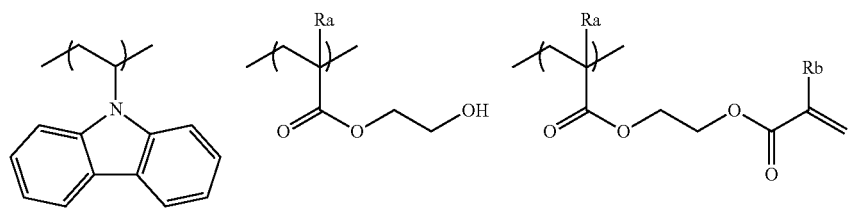
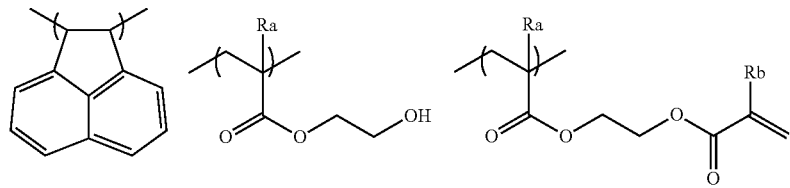
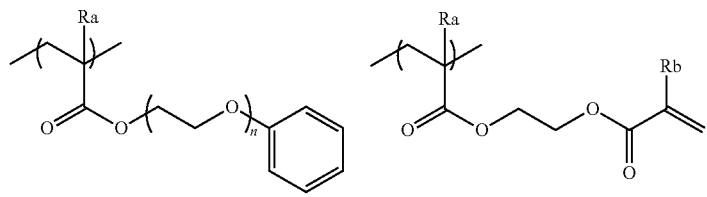

-continued

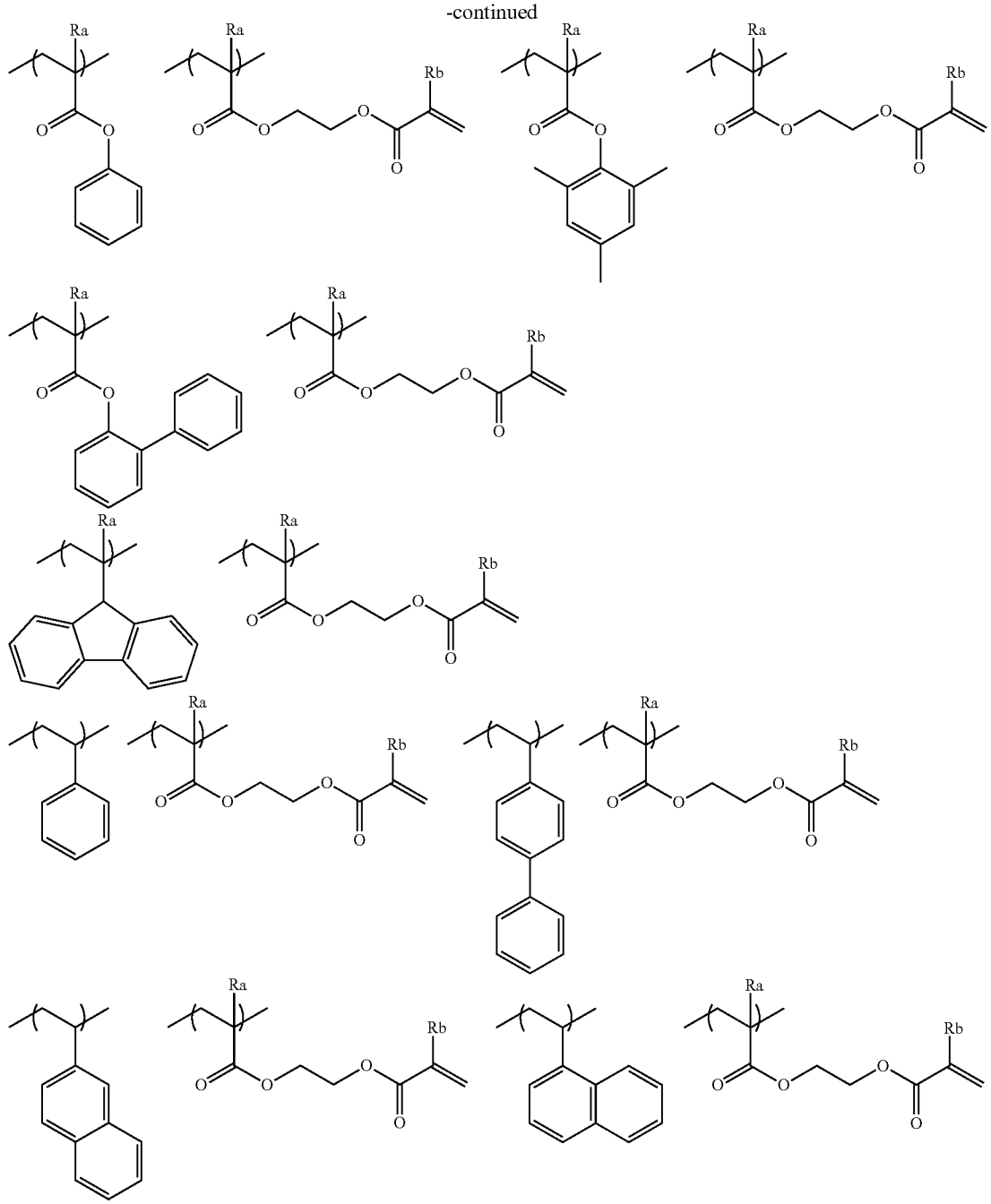

The molecular weight (weight-average molecular weight) of the polymer having a radically polymerizable group in the side chain is preferably 1,000 to 10,000,000, more preferably 5,000 to 300,000, and even more preferably 10,000 to 200,000. The glass transition temperature of the polymer having a radically polymerizable group in the side chain is preferably 50° C. to 400° C., more preferably 70° C. to 350° C., and even more preferably 100° C. to 300° C.

The content of the polymer having a radically polymerizable group in the side chain is preferably 40% by mass or less, more preferably 30% by mass or less, and even more preferably 25% by mass or less with respect to the total mass of the curable composition. The content of the polymer having a radically polymerizable group in the side chain may be 0% by mass, and an aspect in which a polymer having a radically polymerizable group in the side chain is not added is also preferable.

(Other Additives)

Unless contrary to the gist of the present invention, the curable composition may contain additives such as a polymer, a monomer, a dispersant, a plasticizer, a thermal stabilizer, or a mold release agent other than the components described above.

(Viscosity)

The viscosity of the curable composition of the embodiment of the present invention is preferably 20,000 mPa·s or less, more preferably 15,000 mPa·s or less, and even more preferably 13,000 mPa·s or less, and particularly preferably 10,000 mPa·s or less. By setting the viscosity of the curable composition within the above range, it is possible to improve handleability in a case of molding the cured product and forming a high-quality cured product. The viscosity of the curable composition is preferably 2,000 mPa·s or more, more preferably 3,000 mPa·s or more, even more preferably 4,000 mPa·s or more, and particularly preferably 5,000 mPa·s or more.

Method for Manufacturing Cured Product

A cured product can be manufactured by curing the curable composition of the embodiment of the present invention. In a case of manufacturing a cured product, at least one of a photocuring step or a thermal curing step is performed. In addition, in a case of manufacturing a cured product, it is preferable to carry out, in order, a step of forming a semi-cured product by irradiating the curable composition with light or heating the curable composition; and a step of forming a cured product by irradiating the obtained semi-cured product with light or heating the semi-cured product.

(Step of Forming Semi-Cured Product)

The step of forming a semi-cured product preferably includes a transfer step. A transfer step is a step of pressing a mold against the curable composition mentioned above. In the transfer step, the other mold is pressed against the curable composition injected into one of the pair of molds to spread the curable composition.

It is preferable that the mold used with the manufacturing method of cured products is a mold subjected to a chromium nitride treatment. Thereby, a favorable mold releasability can be obtained in a release step to be performed subsequently, and the manufacture efficiency of the optical member can be increased.

Examples of chromium nitride treatment include a method of forming a chromium nitride film on the mold surface. Examples of methods of forming a chromium nitride film on the mold surface include a Chemical Vapor Deposition (CVD) method and a Physical Vapor Deposition (PVD) method. The CVD method is a method of forming a chromium nitride film on a substrate surface by reacting a source gas containing chromium and a source gas containing nitrogen at a high temperature. The PVD method is a method of forming a chromium nitride film on the surface of the substrate using an arc discharge (arc type vacuum deposition method). In this arc type vacuum deposition method, a cathode (evaporation source) made of chromium, for example, is placed in the vacuum vessel, an arc discharge is caused between the cathode and the wall of the vacuum vessel via a trigger, ionization of the metal by arc plasma is performed at the same time as vaporizing the cathode, a negative voltage is applied to the substrate, and about several tens of mTorr (1.33 Pa) of a reaction gas such as nitrogen gas is put into the vacuum vessel, and thereby the ionized metal and the reaction gas are reacted on the surface of the substrate to form a compound film. In the present specification, the chromium nitride treatment on the mold surface is performed by the CVD method or the PVD method.

In general, the mold can be heated while pressing the contents by combining two molds. In a case where a low viscosity composition is injected into the mold, leakage into the mold clearance is caused. For this reason, it is preferable that the curable composition inject into a mold has a certain viscosity or more. In order to adjust the viscosity of the curable composition, a polymer having the above-described radically polymerizable group in the side chain may be added to the curable composition.

After the step of pressing the mold, a step of forming a semi-cured product is performed. The semi-cured product can be obtained by semi-curing the curable composition injected into the mold. In the step of forming the semi-cured product, light irradiation or heating is performed. In the present specification, such a step can also be called a semi-curing step.

In the step of forming a semi-cured product, it is preferable that the curable composition of the embodiment of the present invention is subjected to at least one of light irradiation or heating to form a semi-cured product having a complex viscosity of $10^5$ to $10^8$ mPa·s and a frequency of 10 Hz at 25° C.

As used herein, the term "semi-cured product" in the present specification refers to a product obtained by polymerizing a curable composition, which is not completely solid and has fluidity to some extent. A polymer of a curable composition in such a state that its complex viscosity at 25° C. and at a frequency of 10 Hz is $10^5$ to $10^8$ mPa·s is a semi-cured product. That is, those of which the upper limit value of the complex viscosity at 25° C. and at a frequency of 10 Hz is less than $1.0 \times 10^9$ mPa·s are considered to fall within a range of semi-cured products. On the other hand, the term "cured product" refers to a product produced by curing a curable composition by polymerization and is in a state of being completely solid.

The light used in the photoirradiation is preferably ultraviolet light or visible light and more preferably ultraviolet light. For example, a metal halide lamp, a low pressure mercury lamp, a high pressure mercury lamp, an ultrahigh pressure mercury lamp, a germicidal lamp, a xenon lamp, or a light emitting diode (LED) light source lamp is suitably used. The atmosphere during photoirradiation is preferably air or an inert gas purged atmosphere and is more preferably an atmosphere purged with nitrogen until an oxygen concentration becomes 1% or less.

In a case of providing a heating and semi-curing step in the semi-curing step, the semi-curing by heating is carried out so that the complex viscosity of the semi-cured product at 25° C. and at a frequency of 10 Hz after heating is preferably $10^5$ to $10^8$ mPa·s.

The present invention may relate to a semi-cured product manufactured by the above-described method. Such a semi-cured product may be preferably used for a method for manufacturing a cured product to be described later. The preferred range of the complex viscosity of the semi-cured product is the same as the preferred range of the complex viscosity of the semi-cured product in the above-described step of forming a semi-cured product.

The semi-cured product may not contain the photoradical polymerization initiator at all after the photoirradiation step, since the initiator is completely consumed in the step, or the photoradical polymerization initiator may remain in the semi-cured product.

In addition, the glass transition temperature of the semi-cured product is preferably −150° C. to 0° C., more preferably −50° C. to 0° C., and particularly preferably −20° C. to 0° C.

(Step of Forming Cured Product)

The step of forming a cured product preferably includes a thermal polymerization step of putting the semi-cured product in a molding mold for pressure deformation therein, and heating it therein for thermal polymerization to obtain a cured product or a photopolymerization step of photoirradiating the semi-cured product to obtain a cured product. In the present specification, such a step can also be called a curing step. The photoirradiation conditions and the heating conditions in the forming step of a cured product are the same as those in the semi-curing step described above.

In a case where the curing step is a thermal polymerization step, the molding mold used in the polymerization step is also referred to as a thermoforming mold. In general, the thermoforming mold is composed of two molding mold parts and is preferably designed so that contents can be heated under pressure in the combination of the two molding mold parts. In the method for manufacturing a cured product, a metallic mold is more preferably used as the molding mold in the thermal polymerization step to obtain a cured product. The thermoforming mold of the type for use herein is described, for example, in JP2009-126011A. In addition, it is preferable that the mold is a mold subjected to a chromium nitride treatment.

In the thermal polymerization step, the semi-cured product put in a molding mold is deformed under pressure and heated for thermal polymerization to obtain a cured product. Here, pressure deforming and heating may be carried out simultaneously, or heating may be carried out after pressure deforming, or pressure deforming may be carried out after heating. Above all, preferably, pressure deforming and heating are carried out simultaneously. Also preferably, after simultaneous pressure deforming and heating, the product may be further heated at a higher temperature after the pressure applied thereto has become stable.

In the thermal polymerization step, the semi-cured product is heated and cured at a temperature of 150° C. or higher to obtain a cured product.

The heating temperature is 150° C. or higher, preferably 160° C. to 270° C., more preferably 165° C. to 250° C., and even more preferably 170° C. to 230° C.

In this curing step, it is preferable to perform heating and pressure deformation. Thereby, the inverted shape of the inner surface of the mold can be accurately transferred to the cured product.

The pressure in the pressure deformation is preferably 0.098 MPa to 9.8 MPa, more preferably 0.294 MPa to 4.9 MPa, and particularly preferably 0.294 MPa to 2.94 MPa.

The time of thermal polymerization is preferably 30 to 1000 seconds, more preferably 30 to 500 seconds, and particularly preferably 60 to 300 seconds. The atmosphere during thermal polymerization is preferably air or an inert gas purged atmosphere and more preferably an atmosphere purged with nitrogen until an oxygen concentration becomes 1% or less.

A release step is provided after the curing step. When thermal polymerization is performed in the curing step, it is preferable that the mold is separated from the cured product in a temperature range of 150° C. to 250° C. in the mold release step. By setting the temperature in the mold release step within the above range, the mold can be easily separated from the cured product, and the manufacture efficiency can be increased.

As mentioned above, although an example of the manufacturing method of the cured product of the embodiment of the present invention was described, the structure of the present invention is not restricted thereto, and it can be suitably changed within the range which does not deviate from the present invention. For example, the mold used in the transfer step and the semi-curing step may be used as it is in the curing step; or after performing the semi-curing step, the mold may be pulled away from the semi-cured product, and the semi-cured product may be moved to another mold (thermoforming mold) to perform the curing step. In this case, it is preferable that the above-described chromium treatment is performed on the mold used in the semi-curing step and the curing step.

Furthermore, in the semi-curing step, the curable composition in the mold may be irradiated with light and heated. Thereby, the semi-cured product which has a desired degree of curing can be obtained reliably. The semi-cured product preferably has a complex viscosity of $10^5$ to $10^8$ mPa·s and a frequency of 10 Hz at 25° C.

Cured Product

The cured product of the embodiment of the present invention obtained by curing a curable composition containing the compound represented by General Formula (1) has excellent refractive index characteristics and moisture-heat resistance. That is, the cured product of the embodiment of the present invention has a high refractive index (nd), a low Abbe number (vd), and a high partial dispersion ratio (θg, F).

The Abbe number (vd) of the cured product of the embodiment of the present invention is not particularly limited, but is preferably 30 or less, more preferably 27 or less, even more preferably 25 or less, and particularly preferably 23 or less. By keeping the Abbe number (vd) low, chromatic aberration can be corrected over a wide wavelength range.

In addition, the partial dispersion ratio (θg, F) of the cured product of the embodiment of the present invention is not particularly limited, but is preferably 0.68 or more, more preferably 0.70 or more, and even more preferably 0.72 or more. By increasing the partial dispersion ratio (θg, F), it is possible to effectively correct chromatic aberration particularly at a short wavelength.

The cured product of the embodiment of the present invention is also excellent in moisture-heat resistance. Therefore, it can be effectively used for a lens that may be used under high temperature and high humidity.

The cured product of the embodiment of the present invention preferably has a maximum thickness of 0.1 to 10 mm. The maximum thickness is more preferably 0.1 to 5 mm, and particularly preferably 0.15 to 3 mm. The cured product of the embodiment of the present invention preferably has a maximum diameter of 1 to 1000 mm. The maximum diameter is more preferably 2 to 200 mm, and particularly preferably 2.5 to 100 mm.

Optical Member

The present invention also relates to an optical member including the above-described cured product. Since the cured product of the embodiment of the present invention is a molded object excellent in the optical characteristic, it is preferably used for an optical member. The type of the optical member of the embodiment of the present invention is not particularly limited. In particular, the cured product according to the embodiment of the present invention is suitably used for optical members that utilize the excellent optical properties of curable compositions, especially for light-transmissive optical members (so-called passive optical members). Examples of optically-functional devices equipped with such optical members include various types of display devices (a liquid crystal display, a plasma display, and the like), various types of projector devices (an overhead projector (OHP), a liquid crystal projector, and the like), optical fiber communication systems (a light waveguide, a light amplifier, and the like), and imaging devices such as a camera and a video.

Examples of the passive optical members for use in optically-functional devices include lenses, prisms, prism sheets, panels (plate-like molded bodies), films, optical waveguides (film-like optical waveguide, a fiber-like optical waveguide, and the like), optical discs, and LED sealants. If desired, the passive optical members may be provided with an optional coating layer, such as a protective layer for preventing mechanical damage of the coating surface by friction or abrasion, a light-absorbing layer for absorbing the light having an undesirable wavelength to cause degradation of inorganic particles, substrates and others, a blocking layer for suppressing or preventing permeation of reactive small molecules such as moisture or oxygen gas, an antiglare layer, an antireflection layer, a layer of low refractive index, or the like, as well as any additional functional layer. Specific examples of the optional coating layer include a transparent conductive film or gas barrier film formed of an inorganic oxide coating layer, and a gas barrier film or hard coating film formed of an organic coating layer. The coating method for forming the coating layer may be any known coating method such as a vacuum deposition method, a CVD method, a sputtering method, a dip coating method, or a spin coating method.

The optical member using the cured product of the embodiment of the present invention is especially preferable for a lens substrate. The lens substrate manufactured using the curable composition of the embodiment of the present invention has a low Abbe number and preferably has high refractivity, light transmittance, and lightweight properties, and is excellent in optical properties. By suitably adjusting the type of monomer constituting the curable composition, it is possible to control the refractive index of the lens substrate in any desired manner.

In addition, in the present specification, the "lens substrate" refers to a single member capable of exhibiting a lens function. On and around the surface of the lens substrate, any film and member may be provided depending on the use environment and applications of lenses. For example, a protective film, an antireflection film, a hard coating film, or the like may be formed on the surface of the lens substrate. Further, it can be a compound lens in which a glass lens substrate or a plastic lens substrate is laminated. It is also possible to make the periphery of the lens substrate intrude and be fixed in a substrate holding frame. However, those films and frames are additional members to the lens substrate and therefore differ from the lens substrate itself referred to in the present specification.

In a case of using the lens substrate for lenses, the lens substrate itself may be used as a lens by itself, or additional films or frames or additional lens substrates may be added thereto for use as a lens, as mentioned above. The type and the shape of the lens using the lens substrate are not particularly limited.

The lens substrate is preferably used for, for example, lenses for imaging devices such as mobile phones or digital cameras; lenses for movie devices such as TV or video cameras; and lenses for in-vehicle devices or endoscope lenses.

EXAMPLES

Hereinafter, the features of the present invention will be more specifically described with reference to Examples and Comparative Examples. The material type, the amount of material used, the processing content, the processing procedure, and the like described in the examples can be appropriately changed without departing from the gist of the present invention. Accordingly, the scope of the present invention should not be limitedly interpreted by the following specific Examples.

Synthesis of Compounds

Example 1

Synthesis of Compound A-2

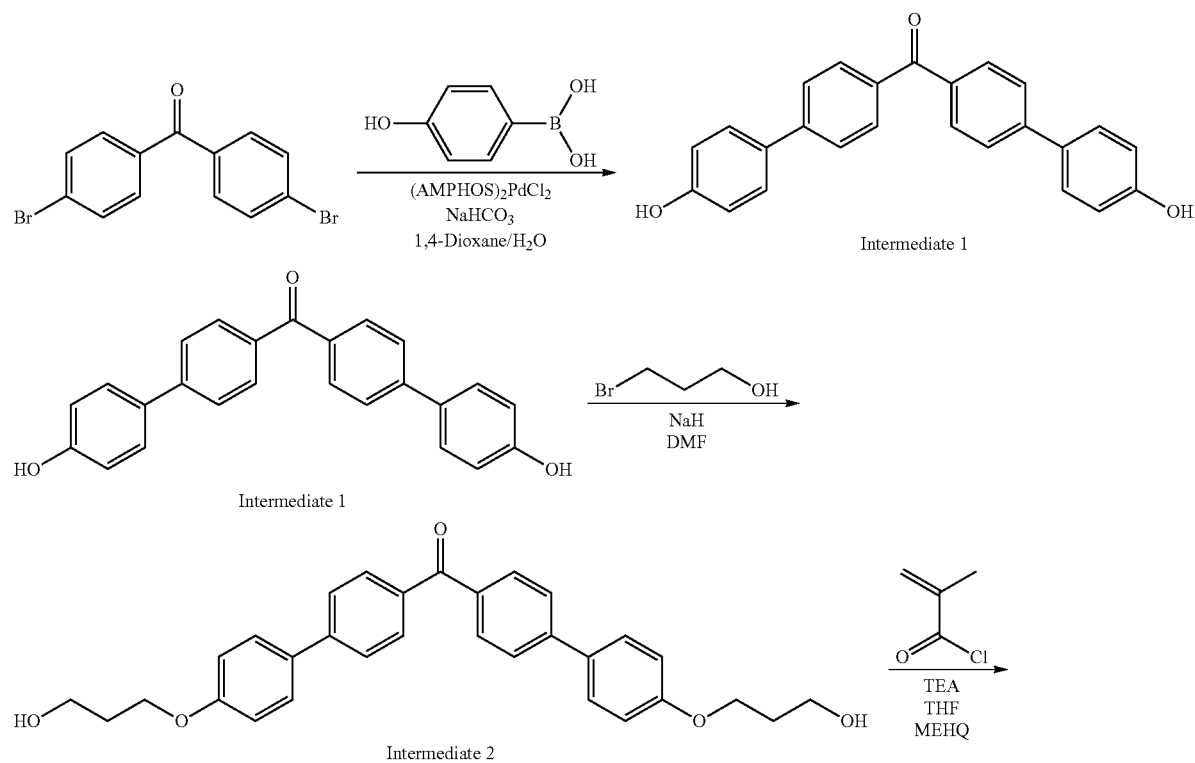

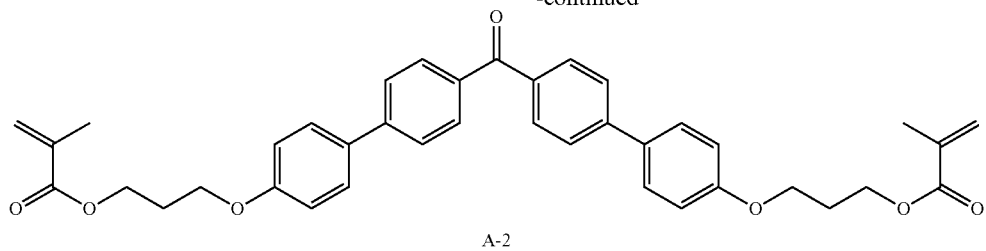

A-2

(1-1) Synthesis of Intermediate 1

To a 1 L three-neck flask, 6.8 g of 4,4'-dibromobenzophenone, 8.3 g of p-hydroxyphenylboronic acid, 200 mL of 1,4-dioxane, and 100 mL of an aqueous solution of saturated sodium bicarbonate was added under a nitrogen stream, and stirred at room temperature for 30 minutes. Thereafter, 0.6 g of bis(di-t-butyl(4-dimethylaminophenyl)phosphine)dichloropalladium (II) [(AMPHOS)$_2$PdCl$_2$] was added, and the reaction was carried out at 90° C. for 3 hours. After confirming the progress of the reaction by thin layer chromatography (TLC), the reaction solution was cooled to room temperature. The precipitated solid was collected by filtration and dissolved in tetrahydrofuran. Silica gel filtration was performed, and hexane was added to the filtrate for recrystallization to obtain 6.7 g of an intermediate 1.

(1-2) Synthesis of Intermediate 2

To a 200 mL three-neck flask, 40 mL of dimethylformamide (DMF) and 0.48 g (oily, 60%) of sodium hydride (NaH) were added and stirred in an ice bath for 10 minutes. 2.0 g of the intermediate 1 was added thereto and stirred at room temperature for 1 hour, and then 1.7 g of 3-bromo-1-propanol was added. The temperature was raised to 50° C., and after 4 hours, a small amount of water was added to stop the reaction. The reaction mixture was diluted with ethyl acetate, washed with water and saturated saline, and the organic layer was dried over magnesium sulfate. Magnesium sulfate was removed by filtration, and hexane was added to the filtrate for recrystallization, thereby obtaining 1.0 g of an intermediate 2.

(1-3) Synthesis of Compound A-2

1.0 g of the intermediate 2, 10 mg of p-methoxyphenol (MEHQ), 10 mL of tetrahydrofuran (THF), and 1.6 mL of triethylamine (TEA) were added to a 100 mL three-neck flask, and stirred in an ice bath for 10 minutes. 1.0 g of methacrylic acid chloride was added thereto and reacted at room temperature for 4 hours, and then a small amount of water was added to stop the reaction. The reaction mixture was diluted with ethyl acetate, washed with water and saturated saline, and the organic layer was dried over magnesium sulfate. Magnesium sulfate was removed by filtration, and hexane was added to the filtrate for recrystallization to obtain 0.6 g of a compound A-2. The data of $^1$H-NMR (Nuclear Magnetic Resonance) of the compound A-2 were as follows.

$^1$H-NMR (300 MHz, DMSO-d$_6$): δ1.88 (s, 6H), 2.05-2.15 ppm (m, 4H), 4.20-4.35 ppm (m, 4H), 4.50-4.65 ppm (m, 4H), 5.70 ppm (s, 2H), 6.05 ppm (s, 2H), 7.00-7.15 ppm (d, 2H), 7.25-7.35 ppm (d, 2H), 7.60-7.80 ppm (m, 8H), 7.85-8.00 ppm (m, 4H)

Example 2

Synthesis of Compound A-4

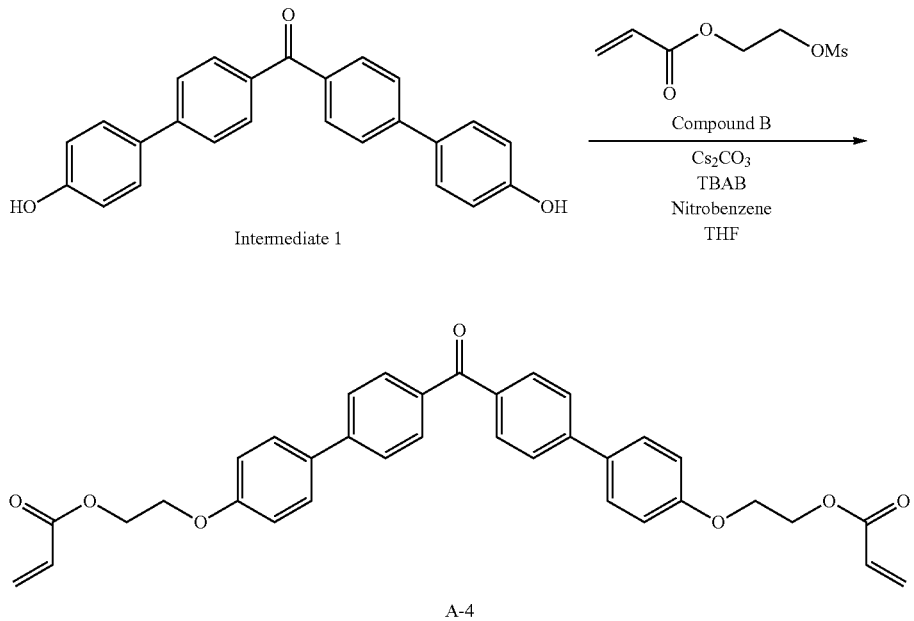

A-4

(2-1) Synthesis of Compound B 100 g of 2-hydroxyethyl acrylate was added to a 2 L three-neck flask, and 132 mL of triethylamine and 650 mL of butyl acetate were added thereto and stirred. While maintaining the reaction solution at 5° C., 70 mL of methanesulfonic acid chloride was added dropwise over 1 hour. After stirring for 1 hour, 500 mL of water was added to the reaction solution, followed by stirring, and the operation of removing the water layer was repeated three times. Subsequently, 30 mg of dibutylhydroxytoluene was added and then the pressure of the reaction system was reduced to distill the butyl acetate to obtain 160 g of a compound B.

(2-2) Synthesis of Compound A-4

To a 500 mL three-neck flask, 5.0 g of the intermediate 1, 50 mL of tetrahydrofuran (THF), 0.05 mL of nitrobenzene, 13.3 g of cesium carbonate ($Cs_2CO_3$), and 0.4 g of tetrabutylammonium bromide (TBAB) was added and stirred.

9.0 g of the compound B was added thereto and reacted for 5 hours while maintaining at 80° C. After cooling the reaction solution to room temperature, 300 mL of water was added, and the precipitated crude crystals were collected by filtration. The crude crystals were dissolved in tetrahydrofuran and recrystallized from methanol to obtain 6.5 g of a compound A-4. The data of $^1$H-NMR (Nuclear Magnetic Resonance) of the compound A-4 were as follows.

$^1$H-NMR (300 MHz, DMSO-$d_6$): δ4.22-4.38 ppm (m, 4H), 4.55-4.70 ppm (m, 4H), 5.80-5.95 ppm (d, 2H), 6.15-6.30 ppm (m, 2H), 6.45-6.55 ppm (d, 2H), 7.00-7.15 ppm (d, 2H), 7.25-7.35 ppm (d, 2H), 7.60-7.80 ppm (m, 8H), 7.85-8.00 ppm (m, 4H)

Example 3

Synthesis of Compound A-6

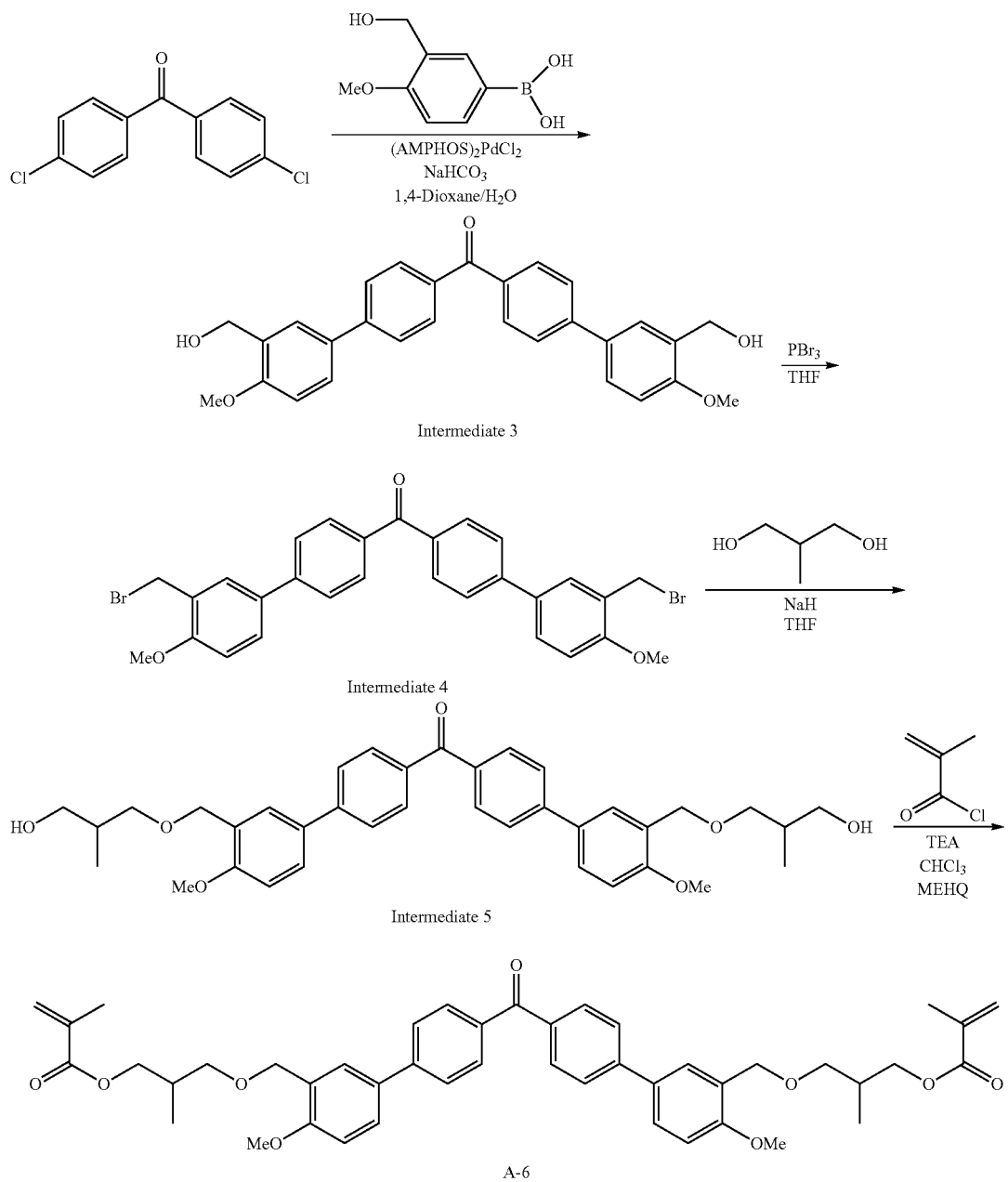

(3-1) Synthesis of Intermediate 3

To a 200 mL three-neck flask, under nitrogen stream, 2.0 g of 4,4'-dichlorobenzophenone, 4.4 g of 3-hydroxymethyl-4-methoxyphenylboronic acid, 40 mL of 1,4-dioxane, and 40 mL of an aqueous solution of saturated sodium bicarbonate were added, and the mixture was stirred at room temperature for 30 minutes. Thereafter, 0.2 g of bis(di-t-butyl(4-dimethylaminophenyl)phosphine)dichloropalladium (II) [(AMPHOS)$_2$PdCl$_2$] was added, and the reaction was carried out at 90° C. for 3 hours. After confirming the progress of the reaction by thin layer chromatography (TLC), the reaction solution was cooled to room temperature, water was added, and the precipitated solid was collected by filtration. The obtained crude crystals were stirred in methanol and washed to obtain 3.5 g of an intermediate 3.

(3-2) Synthesis of Intermediate 4

Under a nitrogen stream, 3.3 g of the intermediate 3 and 60 mL of tetrahydrofuran (THF) were added into a 200 mL three-neck flask and stirred in an ice bath for 10 minutes. 7.0 g of phosphorus tribromide (PBr$_3$) was added thereto and reacted at room temperature for 4 hours, and then a small amount of water was added to stop the reaction. The precipitated crude crystals were collected by filtration and washed with methanol and ethyl acetate to obtain 3.5 g of an intermediate 4.

(3-3) Synthesis of Intermediate 5

To a 200 mL three-neck flask, 40 mL of tetrahydrofuran (THF) and 0.56 g (oil-based, 60%) of sodium hydride (NaH) were added. After cooling in an ice bath, 3 mL of a tetrahydrofuran solution of 1.6 g of 2-methyl-1,3-propanediol was added and stirred at room temperature. After 1 hour, 2.5 g of the intermediate 4 was added and reacted at 60° C. for 3 hours. After cooling to room temperature, the reaction mixture was diluted with ethyl acetate, washed with water and saturated saline, and the organic layer was dried over magnesium sulfate. Magnesium sulfate was removed by filtration, and hexane was added to the filtrate for recrystallization to obtain 2.3 g of an intermediate 5.

(3-4) Synthesis of Compound A-6

To a 100 mL three-neck flask, 1.8 g of the intermediate 5, 10 mg of p-methoxyphenol (MEHQ), 20 mL of chloroform, and 3.0 mL of triethylamine (TEA) were added and stirred in an ice bath for 10 minutes. 2.0 g of methacrylic acid chloride was added thereto and reacted at room temperature for 4 hours, and then a small amount of water was added to stop the reaction. The reaction mixture was diluted with ethyl acetate, washed with water and saturated saline, and the organic layer was dried over magnesium sulfate. After removing magnesium sulfate by filtration, the residue was purified by silica gel column chromatography using hexane/ethyl acetate as a developing solvent to obtain 1.3 g of a compound A-6. The data of $^1$H-NMR (Nuclear Magnetic Resonance) of the compound A-6 were as follows.

$^1$H-NMR (300 MHz, DMSO-d$_6$): δ0.92-1.00 (d, 6H), 1.85 (s, 6H), 2.10-2.20 ppm (m, 2H), 3.40-3.50 ppm (m, 4H), 3.85 ppm (s, 6H), 4.00-4.20 ppm (m, 4H), 4.55 ppm (s, 4H), 5.60 ppm (s, 2H), 6.00 ppm (s, 2H), 7.10-7.20 ppm (d, 2H), 7.65-7.75 ppm (m, 4H), 7.80-7.90 ppm (m, 8H)

Example 4

Synthesis of Compound A-17

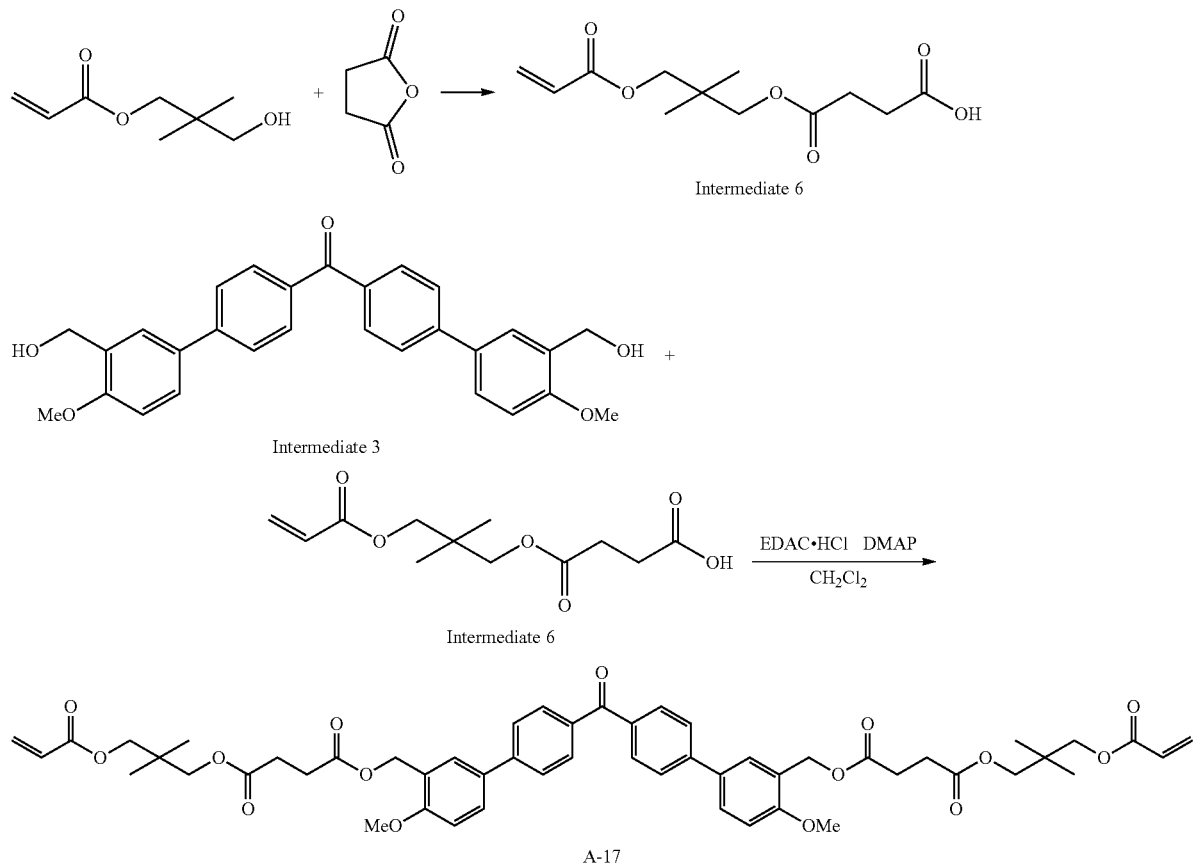

A-17

(4-1) Synthesis of Intermediate 6

40 g of hydroxypropyl acrylate, 300 mL of dichloromethane, 3.8 g of N,N-dimethylaminopyridine, 33.8 g of succinic anhydride, and 200 mg of 2,6-di-t-butyl-4-methylphenol were mixed, and the internal temperature of the mixture was heated to 40° C. After stirring for 12 hours, the mixture was cooled to room temperature, 300 mL of water was added, and the mixture was stirred for 1 hour, followed by liquid separation. The collected organic layer was washed with 1 mol/L hydrochloric acid water and saturated saline, and then dried over anhydrous sodium sulfate. Sodium sulfate was removed by filtration, and the solvent was removed by a rotary evaporator to obtain 70 g of an intermediate 6 which was a transparent oil.

(4-2) Synthesis of Compound 17

To a 300 mL three-neck flask, 9.1 g of the intermediate 3, 11.1 g of the intermediate 6, 240 mg of N,N-dimethylaminopyridine (DMAP), and 100 mL of dichloromethane were added and stirred in an ice bath for 10 minutes. 9.2 g of 1-(3-dimethylaminopropyl)-3-ethylcarbodiimide hydrochloride (EDAC.HCl) was added thereto, and the mixture was reacted at room temperature for 4 hours. The reaction solution was diluted with ethyl acetate, washed with water, an aqueous solution of saturated sodium bicarbonate, and saturated saline in this order, and then the organic layer was dried over magnesium sulfate. After removing magnesium sulfate by filtration, the residue was purified by silica gel column chromatography using hexane/ethyl acetate as a developing solvent to obtain 15.0 g of a compound A-17. The data of $^1$H-NMR (Nuclear Magnetic Resonance) of the compound A-17 were as follows.

$^1$H-NMR (300 MHz, DMSO-$d_6$): δ1.10-1.20 (d, 6H), 2.56-2.68 ppm (m, 8H), 3.88 ppm (s, 6H), 4.00-4.20 ppm (m, 4H), 5.00-5.10 ppm (m, 2H), 5.15 ppm (s, 4H), 5.88-5.96 ppm (m, 2H), 6.05-6.20 ppm (m, 2H), 6.25-6.35 ppm (m, 2H), 7.15-7.25 ppm (d, 2H), 7.70-7.80 ppm (m, 4H), 7.80-7.90 ppm (m, 8H)

Comparative Example 1a

A compound having the following structure was synthesized by the method described in JP2014-043565A. This was designated as a comparative compound 1.

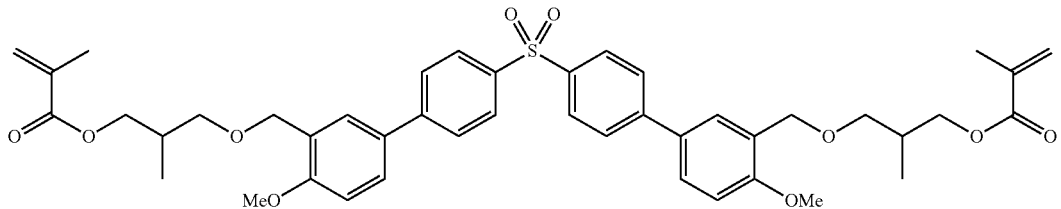 [SMILES: C=C(C)C(=O)OCC(C)COCc1cc(-c2ccc(S(=O)(=O)c3ccc(-c4ccc(OC)c(COCC(C)COC(=O)C(=C)C)c4)cc3)cc2)ccc1OC]

Evaluation of Refractive Index Characteristics of Compounds

Each compound obtained in Examples 1 to 4 and Comparative Example 1 was dissolved in propylene glycol monomethyl ether acetate. At this time, the concentration of each compound was adjusted to be in the range of 1 to 10 weight percent. Each of the obtained solutions was applied onto a quartz substrate by spin coating and dried on a hot plate at 80° C. for 3 hours to produce an optical characteristic evaluation substrate which has a layer with a thickness of 200 to 500 nm. This evaluation substrate is processed into a V-shape, and a refractive index (nF), an Abbe number (vd), and a partial dispersion ratio (θg, F) of each sample were calculated using a Kalnew precision refractometer (manufactured by Shimadzu Device Manufacturing Co., Ltd. KPR-2000). The measurement was performed three times for each sample, and an average value was taken as a measurement result. The results are shown in Table 1.

TABLE 1

| | | Example 1 A-2 | Example 2 A-4 | Example 3 A-6 | Example 4 A-17 | Comparative Example 1 Comparative compound 1 |
|---|---|---|---|---|---|---|
| Compound | | | | | | |
| Evaluation | nd | 1.63 | 1.64 | 1.63 | 1.61 | 1.61 |
| | vd | 18.3 | 18.1 | 16.4 | 17.0 | 20.6 |
| | θg, F | 0.74 | 0.75 | 0.80 | 0.78 | 0.71 |

Thermal curing of curable compositions, and evaluation of refractive index characteristics and evaluation of moisture-heat resistance of thermally cured product Examples 5 to 8 and Comparative Example 2

Preparation of Curable Composition and Thermal Curing

Respective components were added to the above compound so as to have the composition shown in Table 2, and the mixture was stirred to make it homogeneous to prepare a curable composition. The obtained curable composition was poured into a transparent glass mold having a diameter of 20 mm and a thickness of 2 mm, and heated to 200° C. in an atmosphere having an oxygen concentration of 1% or less to produce a thermally cured product. In order to evaluate the characteristics, the sample was processed into a V shape, and a refractive index (nF), an Abbe number (vd), and a partial dispersion ratio (θg, F) of each sample were measured by the same method as in Examples 1 to 4. In addition, according to the following method, evaluation of moisture-heat resistance of each sample was also performed. The results are shown in Table 2.

<Evaluation of Moisture-Heat Resistance>

Each sample whose refractive index (nd) was measured was placed in a constant temperature and humidity chamber maintained at 85° C. and a relative humidity of 85%, stored for 24 hours, and then taken out. Next, after being allowed to stand at 25° C. and relative humidity 60% for 1 hour, a refractive index (nd) was measured, and an amount of change in the refractive index before and after the moisture-heat test was evaluated in the following three grades, A to C.

A: A change in refractive index before and after the moisture-heat test was 0.0005 or less B: A change in refractive index before and after the moisture-heat test was more than 0.0005 and 0.001 or less C: A change in refractive index before and after the moisture-heat test was more than 0.001

PERCUMYL H-80 (manufactured by Nippon Yushi Co., Ltd.)

Cumene hydroperoxide

As shown in Table 1, it was confirmed that Examples 1 to 4 have preferable characteristics because the refractive index (nF) is equal to or higher, the Abbe number (vd) is lower, and the partial dispersion ratio (θg, F) is higher than those of Comparative Example 1.

As shown in Table 2, it was confirmed that Examples 5 to 8 had drastically improved moisture-heat resistance compared to Comparative Example 2. In addition, in the comparison between Examples 7 and 8 and Comparative Example 2 in which the amount of copolymerized monomer is the same, it was confirmed that Examples 7 and 8 have preferable characteristics because the refractive index (nF) is equal to higher, the Abbe number (vd) is lower, and the partial dispersion ratio (θg, F) is higher than those of Comparative Example 2.

Manufacture of Lens

Example 9

Manufacture of Compound Lens 200 mg of the curable composition obtained in Example 7 was injected into a molding mold whose surface was treated with chromium nitride (the surface in contact with the curable composition had an aspheric shape), the entire surface of the curable composition that is not in contact with the molding mold was covered with a transparent glass lens (glass material BK-7, convex lens with a diameter of 33 mm, a center thickness of 3 mm, a radius of curvature of the surface in contact with the curable composition=44.3 mm, a radius of curvature of the surface not in contact with the curable composition=330.9 mm), and the curable composition was expanded to have a diameter of 30 mm. After this

TABLE 2

| | | Example 5 | Example 6 | Example 7 | Example 8 | Comparative Example 2 |
|---|---|---|---|---|---|---|
| Compound of General Formula (1) or comparative compound | A-2 | 45.9 | | | | |
| | A-6 | | 45.9 | 60.9 | | |
| | A-17 | | | | 60.9 | |
| | Comparative compound 1 | | | | | 60.9 |
| Other (meth)acrylate monomers | Phenoxyethyl acrylate | 47.8 | 47.8 | 32.8 | 32.8 | 32.8 |
| Polymerization control agent | β-Caryophyllene | 4.5 | 4.5 | 4.5 | 4.5 | 4.5 |
| Photoradical polymerization initiator | IRGACURE 819 | 0.1 | 0.1 | 0.1 | 0.1 | 0.1 |
| Thermal radical polymerization initiator | Perbutyl O | 1.0 | 1.0 | 1.0 | 1.0 | 1.0 |
| | PERCUMYL H-80 | 0.7 | 0.7 | 0.7 | 0.7 | 0.7 |
| Evaluation | nd | 1.582 | 1.581 | 1.596 | 1.583 | 1.583 |
| | vd | 26.2 | 23.8 | 20.7 | 21.7 | 25.4 |
| | θg, F | 0.70 | 0.75 | 0.77 | 0.75 | 0.68 |
| | Moisture-heat resistance | A | A | A | A | C |

An amount of each component shown in Table 2 is expressed in % by mass. The details of the photopolymerization initiator and thermal polymerization initiator shown in Table 2 are as follows.

IRGACURE 819 (manufactured by BASF)
Bis(2,4,6-trimethylbenzoyl)phenylphosphine oxide
Perbutyl O (manufactured by Nippon Yushi Co., Ltd.)
t-Butylperoxy 2-ethylhexanoate state, the curable composition was semi-cured by being irradiated with 300 mJ/cm$^2$ ultraviolet light from above the glass lens using Execure 3000 (manufactured by HOYA Corporation). Next, while maintaining the state sandwiched between the molding mold and the glass lens, the temperature was raised to 200° C. while applying a pressure of 0.196 MPa (2 kgf/cm$^2$) to the curable composition to further performing curing. Subsequently, after cooling the mold temperature to 180° C., the cured product of the curable composition and the molding mold were separated at a speed of 0.05 mm/second to manufacture a compound lens.

What is claimed is:

1. A curable composition comprising:
a compound represented by General Formula (2):

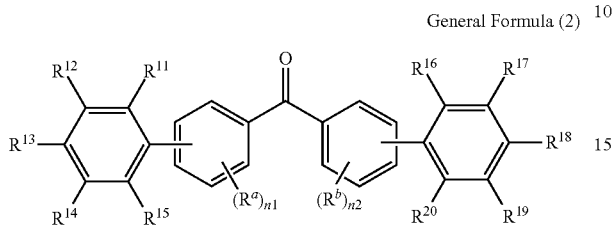

General Formula (2)

in General Formula (2),
$R^a$ and $R^b$ each independently represent a hydroxyl group, an alkyl group, an alkoxy group, and an alkylthio group,
n1 and n2 each independently represent an integer of 0 to 4, in which in a case where n1 is 2 or more, a plurality of $R^a$'s may be the same as or different from each other, and in a case where n2 is 2 or more, a plurality of $R^b$'s may be the same as or different from each other,
$R^{11}$ to $R^{20}$ each independently represent a hydrogen atom, a halogen atom, a hydroxyl group, an alkyl group, an alkenyl group, an alkoxy group, an alkylthio group, an acyl group, an acyloxy group, an alkoxycarbonyl group, an aryl group, a heteroaryl group, an aryloxy group, a heteroaryloxy group, an aryloxycarbonyl group, a heteroaryloxycarbonyl group, an arylthio group, a heteroarylthio group, a cyano group, and an amino group,
at least one of $R^{11}, \ldots,$ or $R^{15}$ is a substituent represented by General Formula (4), and
$R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, and $R^{19}$ and $R^{20}$; two $R^a$'s respectively bonded to adjacent cyclic-skeleton-forming atoms of a benzene ring; and two $R^b$'s respectively bonded to adjacent cyclic-skeleton-forming atoms of a benzene ring each may be bonded to each other to form a linking group necessary to form a cyclic structure, where, a molecule represented by General Formula (2) does not include a polycyclic structure in which three or more aromatic rings are condensed, $$Ac(-L^1-L^2)_{m1}(-L^3)_{m2}-*$$ General Formula (4)

in General Formula (4),
Ac represents a (meth)acryloyloxy group,
$L^1$ represents an alkylene group that has 1 to 6 carbon atoms and may have a substituent selected from a halogen atom, a hydroxyl group, an alkyl group, an alkenyl group, an alkoxy group, an alkylthio group, an acyl group, an acyloxy group, an alkoxycarbonyl group, an aryl group, a heteroaryl group, an aryloxy group, a heteroaryloxy group, an aryloxycarbonyl group, a heteroaryloxycarbonyl group, an arylthio group, a heteroarylthio group, a cyano group, and an amino group,
$L^2$ represents a carbonyl group, an ether group, a thiocarbonyl group, a thioether group, or a linking group that is a combination of these groups,
$L^3$ represents an alkylene group that has 1 to 6 carbon atoms and may have a substituent selected from a halogen atom, a hydroxyl group, an alkyl group, an alkenyl group, an alkoxy group, an alkylthio group, an acyl group, an acyloxy group, an alkoxycarbonyl group, an aryl group, a heteroaryl group, an aryloxy group, a heteroaryloxy group, an aryloxycarbonyl group, a heteroaryloxycarbonyl group, an arylthio group, a heteroarylthio group, a cyano group, and an amino group,
m1 represents any integer of 0 to 10, in which in a case where m1 is 2 or more, a plurality of $L^1$'s may be the same as or different from each other, and a plurality of $L^2$'s may be the same as or different from each other,
m2 represents 0 or 1, and
* represents a binding site of a substituent represented by General Formula (4).

2. The curable composition according to claim 1, wherein $R^{12}$ is a substituent represented by General Formula (4).

3. The curable composition according to claim 1, wherein at least one of $R^{16}, \ldots,$ or $R^{20}$ is a substituent represented by General Formula (4).

4. The curable composition according to claim 1, wherein $R^{11}$, $R^{15}$, $R^{16}$, and $R^{20}$ are hydrogen atoms.

5. The curable composition according to claim 1, wherein the compound is represented by General Formula (3):

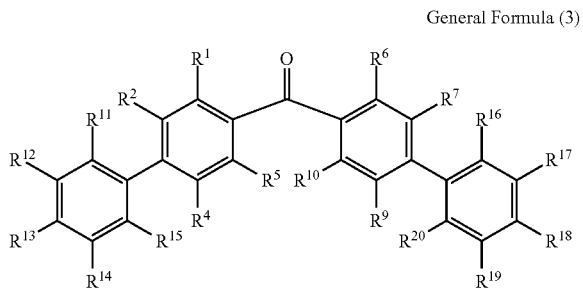

General Formula (3)

in General Formula (3),
$R^1$, $R^2$, $R^4$, $R^5$, $R^6$, $R^7$, $R^9$, and $R^{10}$ each independently represent a hydrogen atom, a hydroxyl group, an alkyl group, an alkoxy group, and an alkylthio group,
$R^{11}$ to $R^{20}$ each independently represent a hydrogen atom, a halogen atom, a hydroxyl group, an alkyl group, an alkenyl group, an alkoxy group, an alkylthio group, an acyl group, an acyloxy group, an alkoxycarbonyl group, an aryl group, a heteroaryl group, an aryloxy group, a heteroaryloxy group, an aryloxycarbonyl group, a heteroaryloxycarbonyl group, an arylthio group, a heteroarylthio group, a cyano group, and an amino group,
at least one of $R^{11}, \ldots,$ or $R^{15}$ is a substituent represented by General Formula (4), and
$R^1$ and $R^2$, $R^4$ and $R^5$, $R^6$ and $R^7$, $R^9$ and $R^{10}$, $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, and $R^{19}$ and $R^{20}$ each may be bonded to each other to form a linking group necessary to form a cyclic structure, where, a molecule represented by General Formula (3) does not include a polycyclic structure in which three or more aromatic rings are condensed.

6. The curable composition according to claim 5, wherein $R^{12}$ is a substituent represented by General Formula (4).

7. The curable composition according to claim 5, wherein at least one of $R^{16}$, ..., or $R^{20}$ is a substituent represented by General Formula (4).

8. The curable composition according to claim 5, wherein $R^{11}$, $R^{15}$, $R^{16}$, and $R^{20}$ are hydrogen atoms.

9. The curable composition according to claim 1, wherein the substituent represented by General Formula (4) is a (meth)acryloyloxyalkoxy group, a (meth)acryloyloxyalkoxyalkyl group, a (meth)acryloyloxyalkoxycarbonylalkyl group, a (meth)acryloyloxyalkoxycarbonylacyloxy group, or a (meth)acryloyloxyalkoxycarbonylacyloxyalkyl group.

10. The curable composition according to claim 1, wherein the compound contains two or more substituents containing a (meth)acryloyloxy group in a molecule.

11. The curable composition according to claim 1, wherein the compound does not contain a polycyclic structure in which two or more aromatic rings are condensed in a molecule.

12. The curable composition according to claim 1, wherein the curable composition contains at least one selected from a photoradical polymerization initiator or a thermal radical polymerization initiator.

13. A semi-cured product of the curable composition according to claim 1.

14. A cured product of the curable composition according to claim 1.

15. An optical member comprising the cured product according to claim 14.

16. A lens comprising the cured product according to claim 14.

17. A compound represented by General Formula (2):

General Formula (2)

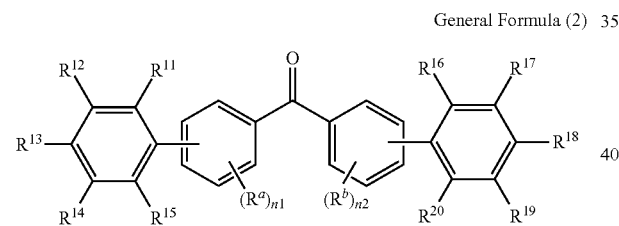

in General Formula (2), $R^a$ and $R^b$ each independently represent a hydroxyl group, an alkyl group, an alkoxy group, and an alkylthio group, n1 and n2 each independently represent an integer of 0 to 4, $R^{11}$ to $R^{20}$ each independently represent a hydrogen atom, a halogen atom, a hydroxyl group, an alkyl group, an alkenyl group, an alkoxy group, an alkylthio group, an acyl group, an acyloxy group, an alkoxycarbonyl group, an aryl group, a heteroaryl group, an aryloxy group, a heteroaryloxy group, an aryloxycarbonyl group, a heteroaryloxycarbonyl group, an arylthio group, a heteroarylthio group, a cyano group, and an amino group, at least one of $R^{11}$, ..., or $R^{15}$ is a substituent represented by General Formula (4), and $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, and $R^{19}$ and $R^{20}$; two $R^a$'s respectively bonded to adjacent cyclic-skeleton-forming atoms of a benzene ring; and two $R^b$'s respectively bonded to adjacent cyclic-skeleton-forming atoms of a benzene ring each may be bonded to each other to form a linking group necessary to form a cyclic structure, where, a molecule represented by General Formula (2) does not include a polycyclic structure in which three or more aromatic rings are condensed, $$Ac(-L^1-L^2)_{m1}(-L^3)_{m2}-* \qquad \text{General Formula (4)}$$

in General Formula (4),

Ac represents a (meth)acryloyloxy group, $L^1$ represents an alkylene group that has 1 to 6 carbon atoms and may have a substituent selected from a halogen atom, a hydroxyl group, an alkyl group, an alkenyl group, an alkoxy group, an alkylthio group, an acyl group, an acyloxy group, an alkoxycarbonyl group, an aryl group, a heteroaryl group, an aryloxy group, a heteroaryloxy group, an aryloxycarbonyl group, a heteroaryloxycarbonyl group, an arylthio group, a heteroarylthio group, a cyano group, and an amino group, $L^2$ represents a carbonyl group, an ether group, a thiocarbonyl group, a thioether group, or a linking group that is a combination of these groups, $L^3$ represents an alkylene group that has 1 to 6 carbon atoms and may have a substituent selected from a halogen atom, a hydroxyl group, an alkyl group, an alkenyl group, an alkoxy group, an alkylthio group, an acyl group, an acyloxy group, an alkoxycarbonyl group, an aryl group, a heteroaryl group, an aryloxy group, a heteroaryloxy group, an aryloxycarbonyl group, a heteroaryloxycarbonyl group, an arylthio group, a heteroarylthio group, a cyano group, and an amino group, m1 represents any integer of 0 to 10, in which in a case where m1 is 2 or more, a plurality of $L^1$'s may be the same as or different from each other, and a plurality of $L^2$'s may be the same as or different from each other, m2 represents 0 or 1, and

* represents a binding site of a substituent represented by General Formula (4).

* * * * *